US011000225B2

(12) United States Patent
Lei et al.

(10) Patent No.: US 11,000,225 B2
(45) Date of Patent: May 11, 2021

(54) INTEGRATED CIRCUIT FOR SIMULTANEOUS ELECTROPHYSIOLOGY RECORDING AND OPTOGENETIC NEURAL CONTROL

(71) Applicants: The Regents of the University of Colorado, Denver, CO (US); University of Macau, Taipa (MO)

(72) Inventors: Tim Lei, Thornton, CO (US); Achim Klug, Denver, CO (US); Sio Hang Pun, Macau (CN); Changhao Chen, Englewood, CO (US); Mang I. Vai, Macau (CN); Peng Un Mak, Macau (CN); Elizabeth McCullagh, Fort Collins, CO (US)

(73) Assignees: The Regents of the University of Colorado, Denver, CO (US); University of Macau, Taipa (MO)

( * ) Notice: Subject to any disclaimer, the term of this patent is extended or adjusted under 35 U.S.C. 154(b) by 191 days.

(21) Appl. No.: 16/024,217

(22) Filed: Jun. 29, 2018

(65) Prior Publication Data
US 2019/0000377 A1    Jan. 3, 2019

Related U.S. Application Data

(60) Provisional application No. 62/526,734, filed on Jun. 29, 2017.

(51) Int. Cl.
| | |
|---|---|
| *A61B 5/00* | (2006.01) |
| *A61B 5/04* | (2006.01) |
| *A61N 5/06* | (2006.01) |

(52) U.S. Cl.
CPC ........ *A61B 5/4836* (2013.01); *A61B 5/04001* (2013.01); *A61B 5/6868* (2013.01);
(Continued)

(58) Field of Classification Search
CPC . A61B 5/4836; A61B 5/04001; A61B 5/6868; A61B 5/7246; A61N 5/0622; A61N 2005/0612; A61N 2005/0626
See application file for complete search history.

(56) References Cited

U.S. PATENT DOCUMENTS

| | | |
|---|---|---|
| 9,238,150 B2 | 1/2016 | Deisseroth et al. |
| 2009/0088680 A1 | 4/2009 | Aravanis et al. |
| | (Continued) | |

OTHER PUBLICATIONS

Hamilton, Lei et al., "Neural Signal Processing and Closed-Loop Control Algorithm Design for an Implanted Neural Recording and Stimulation System," Conference Proceedings for IEEE Engineering in Medicine and Biology Society, pp. 7831-7836, Aug. 2015.

*Primary Examiner* — Lindsey G Wehrheim

(57) ABSTRACT

Various embodiments of the present technology generally relate to a single monolithic IC to perform simultaneous optogenetic neural inhibition and extracellular electrophysiological recording in-vivo. Some embodiments include a low input capacitance (e.g., 9.7 pF) amplifier particularly tailored for the use of high-impedance electrodes to conduct single neuron extracellular recording integrated with programmable high current drivers for optogenetic stimulation or inhibition on the same IC chip. Some embodiments use a noise model to guide the IC design process to obtain parameters for optimal signal-to-noise ratio. The performance of the IC chip was demonstrated on an anesthetized gerbil expressed with inhibitory optogenetic protein (Halorhodopsin). Spontaneous action potentials from the fifth nerve of the brainstem were recorded by the amplifier and were subsequently inhibited by laser illumination. As a result, various embodiments of the IC allow neuroscience research and neural engineering applications to be conducted in an entirely new direction and can potentially be used in treatments for human mental diseases in the future.

20 Claims, 25 Drawing Sheets

(52) U.S. Cl.
CPC .......... *A61B 5/7246* (2013.01); *A61N 5/0622* (2013.01); *A61N 2005/0612* (2013.01); *A61N 2005/0626* (2013.01)

(56) References Cited

U.S. PATENT DOCUMENTS

| | | |
|---|---|---|
| 2009/0093403 A1* | 4/2009 | Zhang .................... A61P 25/00 514/8.1 |
| 2010/0094377 A1 | 4/2010 | Graupe |
| 2011/0301529 A1 | 12/2011 | Zhang et al. |
| 2013/0289669 A1 | 10/2013 | Deisseroth et al. |
| 2014/0113367 A1 | 4/2014 | Deisseroth et al. |
| 2016/0175607 A1 | 6/2016 | Deisseroth et al. |
| 2016/0279267 A1 | 9/2016 | Deisseroth et al. |

\* cited by examiner

INTEGRATED CIRCUIT FOR SIMULTANEOUS ELECTROPHYSIOLOGY RECORDING AND OPTOGENETIC NEURAL CONTROL

CROSS-REFERENCE TO RELATED APPLICATIONS

This application claims priority to U.S. Provisional Application Ser. No. 62/526,734 filed Jun. 29, 2017, which is incorporated herein by reference in its entirety for all purposes.

STATEMENT REGARDING FEDERALLY SPONSORED RESEARCH

This invention was made with government support under grant numbers DC011582, DK095232, 1K25DK095232-01A1 and P30NS048154 awarded by The National Institutes of Health. The government has certain rights in the invention.

BACKGROUND

Electrophysiological recordings of action potentials in the brain have been one of the most important research tools for neuroscientists to decipher the function of neuronal circuits. This class of electronic recording techniques which uses conductive electrodes and low-noise precision amplifiers to monitor voltage signals in the brain gives researchers and neurosurgeons the ability to observe neural signals with great precision. In addition, recent advances in neural stimulation techniques, including direct current injection and activation of optogenetic light-sensitive proteins, make manipulating signals in the brain possible, With these external stimulation techniques, direct intervention of the functioning of neural circuitries can enhance, interrupt, or correct how neural signals are processed.

One such method that recently received much attention is the experimental manipulation of neuronal circuits with light (optogenetics) to control complex neuronal functions, including behavior. Optogenetics is a biomolecular technique in which DNA of light-sensitive ion channels can be introduced into neurons of interest. Light-sensitive ion channels will then be expressed and transported to the cell membrane by the native protein translation mechanisms of the cells. Once introduced into neurons, these light-sensitive ion channels can then be activated by light, and become permeable for either positive (kation) or negative (chloride) ions, depending on the type of optogenetic protein. For example, the blue-light (peaked at ~480 nm) sensitive Channelrhodopsin (ChR) selectively allows positively charged ions to enter neurons and thereby stimulate the firing of action potentials. In contrast, the orange-light (peaked at ~580 nm) sensitive Halorhodopsin (NpHR) is a chloride pump by which negatively charged chloride ions are pumped into neurons, inhibiting action potential firing.

Therefore, by choosing the type of optogenetic protein for transfection and the corresponding wavelength for a light source, action potentials can be selectively triggered or inhibited. In addition, cell type specificity within the neuronal target can be achieved by selecting different promotors, or using genetic approaches such as the Cre-Lox recombination technique. In comparison, controlling neuronal activity via electrical stimulation is much more limited, in that action potentials cannot be inhibited, and the electrical stimulation is not cell type specific. This kind of flexibility makes optogenetics the technique of choice to control neuronal circuits under various experimental conditions, and enables certain types of studies that used to be extremely difficult if not impossible. This technology also has the potential to be translated into future treatment options for neural disorders in human patients.

SUMMARY

Various embodiments of the present technology generally relate to optogenetic neural control. More specifically, some embodiments relate to an integrated circuit that combines neural recording amplifiers and an optogenetic controller that can be used to record neural activity from both live humans and animal models in-vivo while simultaneously controlling neural activity with light that is delivered to deep brain areas via optical fibers or implantable LED sources.

Some embodiments include an integrated circuit for optogenetic control. The integrated circuit can include an interface to receive signals from one or more optrodes measuring a target neuron. The integrated circuit can also include a neural amplifier having multiple stages to receive the signals from the one or more optrodes. The multiple stages of the neural amplifier may include a unity-gain buffer to maximize input impedance from the signals received via the one or more optrodes. In some embodiments, the integrated circuit may also include a programmable optical driver to control a laser to provide optogenetic stimulation or inhibition of the target neuron. The programmable optical driver may include a multi-stage current driver that includes a first stage to provide coarse control and a second stage to provide fine control. The programmable optical driver may include a laser driver and/or a light emitting diode driver.

In some embodiments, the integrated circuit may also include a real-time spike sorting unit configured to use template matching techniques (e.g., Euclidian distance matching process and a correlational matching process) to sort the signals from the one or more optrodes based on spikes. For example, templates may be created by an external host computing system and communicated to the integrated circuit via the communications interface. The integrated circuit of claim 1, further comprising a real-time spike sorting unit that includes multiple template matching processes implemented in hardware on the integrated circuit that can be selectively activated by a user.

In some embodiments, a method for inhibiting or activating neurons within a brain can include measuring, using one or more recording electrodes, neural activity of a brain (e.g., of an animal or human). The neural activity measured using the one or more recording electrodes can be processed to identify neuron firing. Using a controller, a control action can be determined to repattern the neuron firing. The control action can then be implemented in the brain using an optogenetic control system. Some embodiments may also identify and sort spikes within the neural activity measured using the one or more recording electrodes. Using template classification, neural activity from different neurons can be identified. The template classification includes multiple user-selectable options that include a Euclidian distance matching process and a correlational matching process.

The method may also include, receiving, from an external computer, a set of cluster templates to a field programmable gate array (FPGA) or a custom application-specific integrated circuit (ASIC). Using the FPGA or ASIC, spikes can be sorted and decode, either using rate-coding and temporal coding schemes, within the neural activity based on the set of cluster templates. Sorted neural activity can be generated based on the spikes identified locally at an integrated circuit. The controller can be fed the sorted neural activity and use that information to determine the control action to repattern the neuron firing.

In some embodiments, a system can include a power supply (e.g., a rechargeable battery), one or more processors, a neural interface, and a memory. The neural interface can be configured to receive measurements of neural activity from a brain of an animal or human. The memory can have stored thereon instructions that when executed by the one or more processors cause the system to process the measurements of the neural activity from the brain of the animal or human to identify neuron firing, determine a control action to alter the neuron firing, and transmit the control action to an optogenetic laser system to facilitate inhibition or stimulation of neuron firing. The system may also include an FPGA or an ASIC configured to receive the measurements of the neural activity and programmed to sort spikes within the measurements of the neural activity. The system may also include an optrode having one or more electrodes that can be inserted into the brain of the human or animal to collect the measurements of the neural activity that can be transmitted to the neural interface.

The optogenetic laser system may include a multi-stage current controller to translate the control action into a desired light to facilitate the inhibition or stimulation of neuron firing. An external computer may be used in some embodiments to generate a set of cluster templates. The FPGA or ASIC to use the set of cluster templates to classify, in real-time, spikes within the measurements of the neural activity and separate measurements from different neurons.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings in which.

Figure 1:
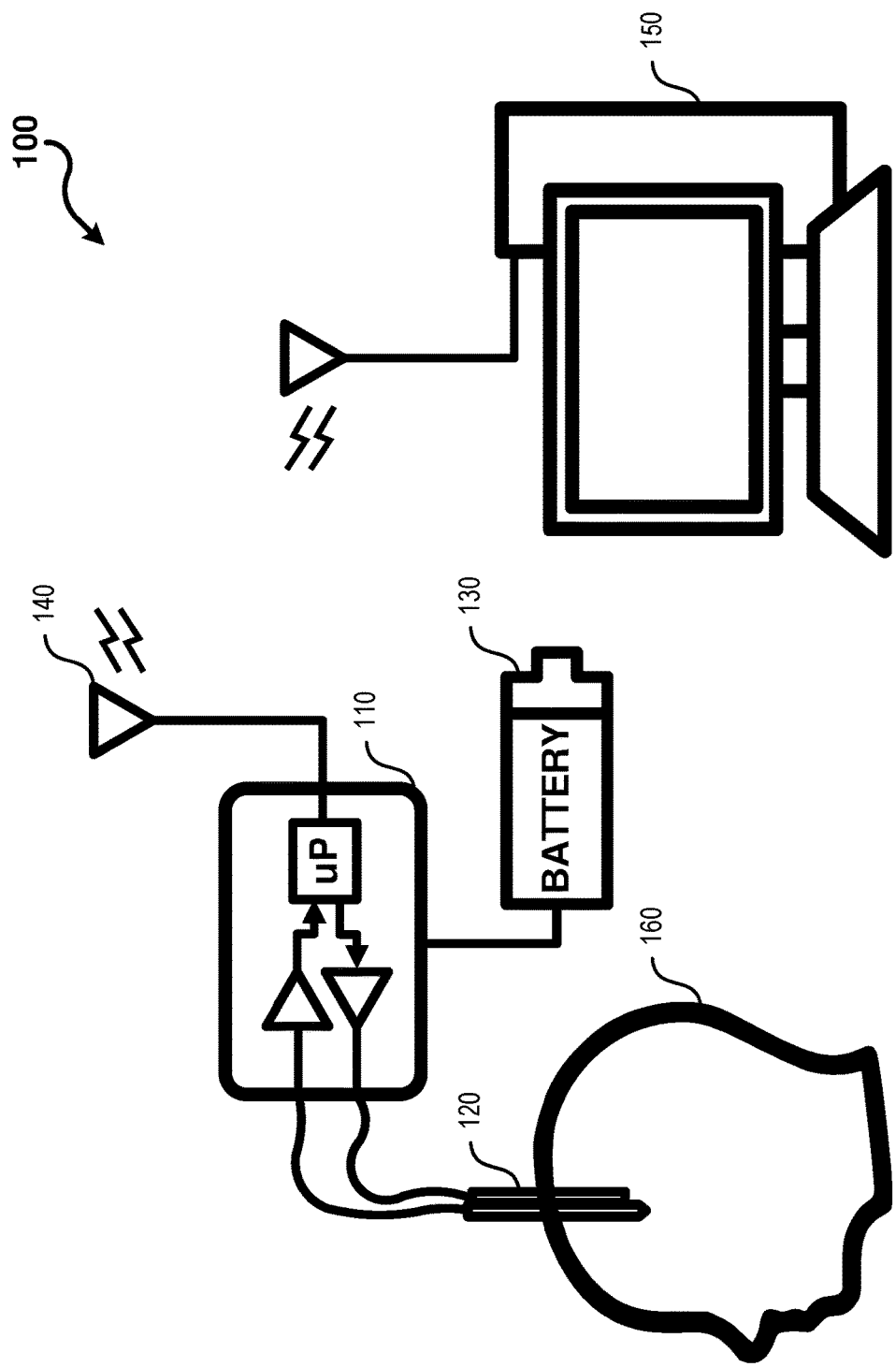
FIG. 1 illustrates an example of a system that combines a low-noise and high input impedance (or low input capacitance) neural recording amplifier, and a high current laser/LED driver in a monolithic integrated circuit (IC) for simultaneous neural recording and optogenetic neural control.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to optogenetic neural control. More specifically, some embodiments relate to an integrated circuit that combines neural recording amplifiers and an optogenetic controller that can be used to record neural activity from both live humans and animal models in-vivo while simultaneously controlling neural activity with light that is delivered to deep brain areas via optical fibers. In order to compute the correct patterns and intensities of light delivery, a CPU may also be included in the device that processes and analyzes the incoming neural activity and responds to the activity patterns with appropriate light activation according to predetermined algorithms.

The ability to record and to manipulate neural circuitries in the brain simultaneously opens up new opportunities to study complex signal pathways of the brain or to treat neural disorders. For example, neural spikes can be measured to calculate the firing rate or the dynamic state vector to estimate the functions of the neural circuit. Optogenetic manipulation can in turn be used to activate or to suppress certain neural targets based on the measured spike data or results obtained by analyzing these spikes. This closed-loop control scheme allows studying complex functions of neural circuitries or arresting onsets of neural disorders by detecting abnormal neural signals.

From a system control standpoint, the electrophysiological recording and the optogenetic control can be considered as the input and the output units of a closed-loop control system, respectively. A processing unit, either integrated into a single integrated circuit together with the input and output units or connected externally, processes the recorded neural spikes to generate appropriate response for the output control unit. Various embodiments of the present technology provide for an electronic system which measures the action potentials extracellularly using a low-noise and high-input impedance amplifier; the data is then processed by a processor using spike sorting processing and decoding routines; finally, the output response is used to inhibit neural firing of a neural target of an animal.

In behavioral studies, it is often technologically challenging to record electrical activity intracellularly, i.e. from inside neurons, while the animal is awake or moving. Therefore, action potentials are generally recorded by placing an electrode outside but very close to the neuron of interest in the extracellular space for in-vivo or behavioral experiments. The electric current induced in the extracellular space is, however, relatively small, and translates into a voltage recorded by the external electrode typically in the sub-mV rang. In addition, the ability to separate signals originating from neighboring neurons from each other is critical, especially for recording from densely packed neurons which have somas typically around 5-15 µm in diameter.

To isolate the weak signals generated by these cells, small recording surface (several micrometers in diameter) electrodes are often used to limit the range of detection, in contrast to local field potential (LFP) recordings or multi-neuron recordings where the recording surface is significantly larger. Electrodes with exposed tips of approximately 100 µm in diameter were estimated to cover a sphere with a radius of 50-350 µm. Small tipped electrodes, however, have a very high electrical impedance (several mega-ohms). This high electrode impedance in turn acts as a voltage divider with the recording amplifier input impedance, which significantly reduces the signal voltage measurable by the recording amplifier. As a result, some embodiments use an amplifier design to achieve a high input impedance, or low input capacitance, for optimized use of high impedance electrodes.

Various embodiments of the present technology include a design of a single monolithic IC which includes a high-impedance and low-noise neural amplifier for extracellular in-vivo recording and an adjustable current driver for simultaneous optogenetic stimulation or inhibition. In addition, some embodiments of the IC allow for simultaneously recording and optogenetically stimulating or inhibiting neurons in the brain. For example, in some embodiments spontaneous neural spiking of the fifth nerve in the brainstem of anesthetized gerbils was successfully recorded in-viva and at the same time inhibited 3-4 fold by optical illumination. Simulations and experimental measurements were also performed to confirm that the neural amplifier has a good signal-to-noise ratio (SNR~6.6) adequate for extracellular in-viva neural recording. The high current LED/laser driver can produce a maximum current of 330 mA capable of driving a 50 mW 532 nm laser for optogenetic neural inhibition.

Generally, inhibiting action potentials is technically more challenging than to excite action potentials because of the higher optical intensity required for optogenetic inhibition (~50 mW/mm² vs ~10 mW/mm²). Therefore, action potentials stimulation should in principle be possible if not technically easier using the same IC, changing the illumination laser source to ~480 nm wavelength and injecting ChR virus to the animals. Other constructs, such as red-shifted constructs may also be used in some embodiments, requiring the use of corresponding lasers or LEDs.

The noise performance in various embodiments of the amplifier design is on par with other state-of-art neural amplifier designs (the input referred noise in one particular design is 4.13 µVrms). Comparatively, the measured input referred noise of various embodiments can be approximately $\sqrt{V_A^2}=4.57~\mu V_{rms}$. The input referred noise of some designs is also much lower than the estimated thermal noise ($\sqrt{V_{Re}^2}\sim 18.2~\mu V_{rms}$) of the 3 MΩ metal electrodes over a 5 kHz bandwidth. In addition, some embodiments of the amplifier may have a low input capacitance optimized for extracellular neural single cell recordings, in contrast to other designs which are optimized for measuring the local field potential or multiple cell firing. The input capacitance of the amplifier may be around 9.3 pF, which is much lower than the typical electric double layer capacitor of a metal electrode (Ce~50 pF). These two parameters satisfy the two requirements in the noise model analysis that 1) $C_{in} \ll C_{e1}$ and 2) $V_A^2 \ll R_{Re}^2/2$. Therefore, the measured ~33 μVpp noise can be attributed to mostly dominating by the thermal noise of the metal electrode, which is the fundamental limiting factor of noise in the electrophysiological recording.

Various embodiments of the present technology combine neural recording and optogenetic control in a single IC; therefore, one or more recording amplifiers and current control units may be integrated in the IC. Some embodiments may also include the use of multi-channel recording and optogenetic control to record neural circuits at several different brain regions to test various hypotheses of brain signal processing.

The combination of neural recording with optogenetic control in a single monolithic IC that is present in various embodiments may allow new experimental designs to answer neuroscience problems previously difficult to answer, or to allow new treatments of neural disorders in the future. For instance, abnormal neural firing just before the onset epileptic seizures can be detected and countered via an optogenetic intervention. In addition, some embodiments also include a wireless data communication model, a miniaturized LED light source, and a small and light-weight battery providing a "backpack" for small rodents or animals. This "wearable" device will allow neuroscientists to conduct electrophysiology recording on animals for long-duration behavioral studies, and also allow manipulation of the neural circuits in real-time.

The measured neural spikes can also be analyzed and processed using a computer processor or digital electronic circuitry. In some embodiments, neural spikes can be sorted using a template matching method programmed into a field-programmable-gate-array (FPGA) as the signal processing unit. Neural spikes can then be sorted on the fly by the FPGA. In some embodiments, the system may achieve a short delay of less than 2 ms to sort the spikes, with a maximum spike sorting rate of 941 spikes/second. The firing rates of each spike cluster groups can also be calculated by the FPGA to provide the necessary control parameters to the control unit. The LED/Laser driver then in turn switch on or off power to the LED/Laser for optogenetic manipulation.

Some embodiments provide for a real-time neural spike sorting using template matching techniques. The system can include a host computer to generate cluster templates and an FPGA to match subsequent incoming spikes to the templates in real time. Two template matching methods are user selectable for best sorting results in which ED is best for sorting spikes contaminated by regular Gaussian noise typically induced by instrumentations and CM is best for other atypical noise, such as positional drift of electrodes.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to optogenetic neural control, embodiments of the present technology are equally applicable to various other neural control technologies.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

FIG. 1 illustrates an example of a system 100 that combines a low-noise and high input impedance (or low input capacitance) neural recording amplifier, and a high current laser/LED driver in a monolithic integrated circuit (IC) 110 for simultaneous neural recording and optogenetic neural control. IC 110 can be powered by battery 130 which may be wirelessly rechargeable in some embodiments. IC 110 can include a transceiver 140 which can be used to wirelessly transmit data and/or receive commands from external computing device 150.

In accordance with various embodiments, the low input capacitance of the amplifier (e.g., approximately 9.7 pF) can be achieved through adding a dedicated unity gain input stage optimized for high impedance metal electrodes. The input referred noise of the amplifier, in some embodiments, was measured to be approximately 4.57 $\mu V_{rms}$, which is lower than the estimated thermal noise of the metal electrode 120. Thus, action potentials originating from a single neuron can be recorded with a signal-to-noise ratio of ~6.6. Some embodiments include a LED/laser current driver to deliver a maximum current (e.g., 330 mA) to generate adequate light for optogenetic control.

Tailoring the input impedances of the amplifiers allows for selective measurements of local filed potentials, action potentials from multiple neurons, or action potentials from a single neuron within a brain of a human or an animal 160. In particular, a high impedance electrode 120 with a small recording surface can be used to record single neuronal activity and designs of neural amplifiers specially tailored for this application are relatively few.

Figure 2:
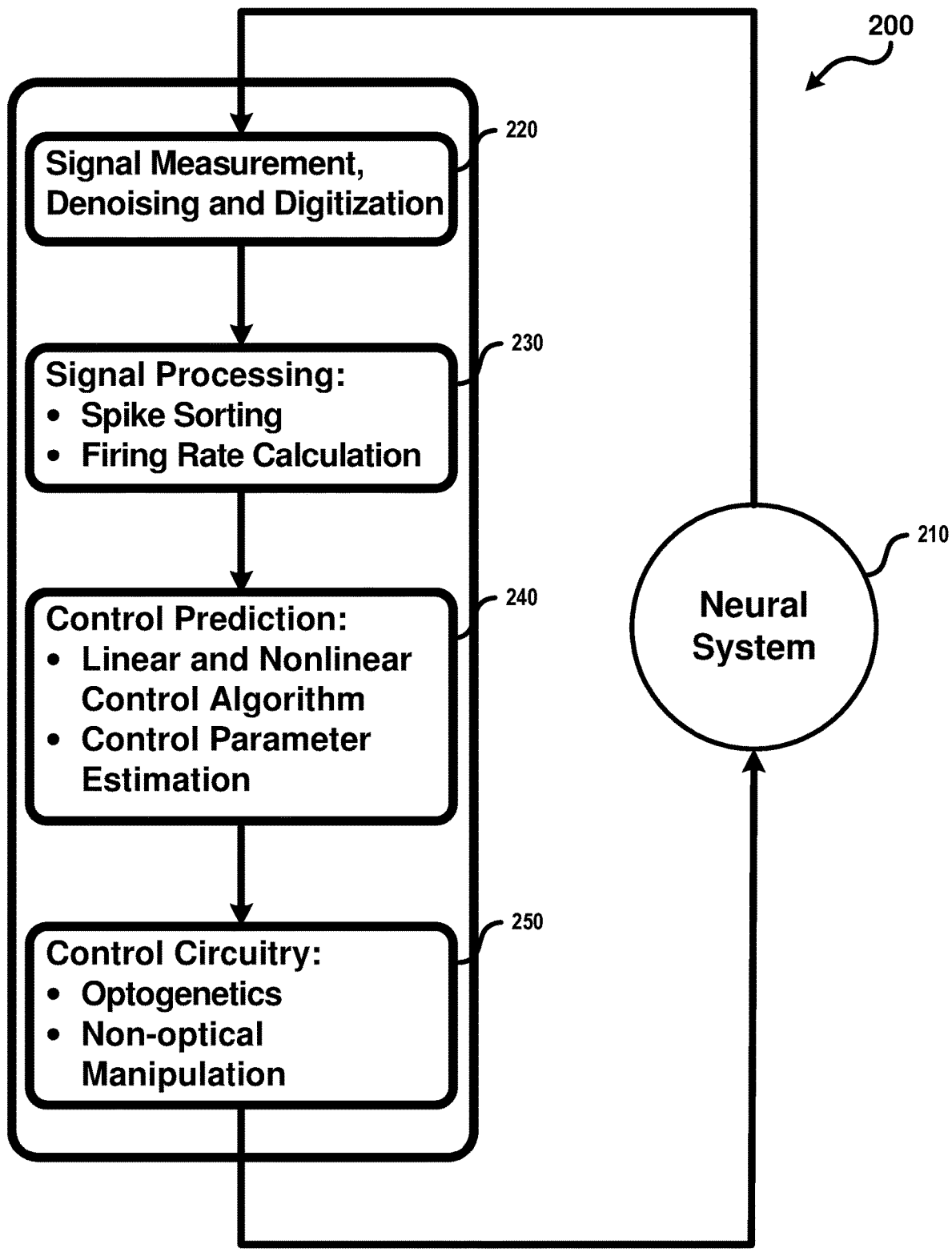
FIG. 2 is a flowchart illustrating an example of a set of operations that can be used for optogenetic control of a neural system in accordance with one or more embodiments of the present technology.

FIG. 2 is a flowchart illustrating an example of a set of operations 200 that can be used for optogenetic control of a neural system 210. As illustrated in FIG. 2, measurement operation 220 receives a measurement signal from neural system 210 and may perform some preprocessing operations such as denoising and digitization of the measurement signal. Processing operation 230 can perform a variety of signal processing, such as but not limited to, spike sorting (described in more detail below), firing rate calculations, and the like. Using this information, control operation 240 can generate one or more control actions (e.g., based on linear control algorithms, nonlinear control algorithms, adaptive control algorithms, and the like) which can be implemented using control system 250. In accordance with some embodiments, control system 250 may include various optogenetic techniques and/or non-optical manipulation. For example, control system 250 can selectively stimulate or inhibit action potentials within neural system 210 by choosing the type of optogenetic protein for transfection and the corresponding wavelength for a light source.

I. OPTOGENETICS AND SIGNAL-TO-NOISE ANALYSIS

A. Optogenetics

The two families of optogenetic proteins—excitatory versions (here for simplicity abbreviated as ChR) and inhibitory versions (here for simplicity abbreviated as NpHR)—have distinctly different optical excitation spectra. ChR and NpHR have maximum absorptions at ~470 nm (blue) and ~580 nm (orange), respectively (but note that other versions such as red-shifted constructs could be used in other embodiments). This spectral separation of 90 nm allows the two proteins to be separately excited using different colors of light even when the two proteins are co-transfected in the same cell. In in-vivo or behavioral experiments, light is typically delivered to neuronal targets through optical fibers. In accordance with various embodiments, the excitation light sources can either be a laser or a light-emitting-diode (LED), provided that the optical power at the fiber output is high enough to activate the optogenetic proteins (optical coherency is not important in the application). Typical optical power density required to excite ChR and NpHR is ~10 mW/mm$^2$ and ~50 mW/mm$^2$, respectively. The brain, however, is high optical scattering and therefore optical scattering in the brain significantly reduces the amount of optical power available for optogenetic excitation.

In some embodiments, optical power required at the fiber tip can be accurately estimated using an iPhone or Android APP based on measured data. For instance, 100 mW of optical power can effectively inhibit about ~800 μm depth of brainstem using NpHR under ideal conditions. Therefore, current drivers capable of delivering hundreds of mA of electric current are necessary to drive laser or LED sources to produce adequate optical power for successful optogenetic controls. The temporal requirement of the current drivers is comparatively simple. Action potentials typically have a pulse duration of a few milli-second with a rise time of several tenths of a milli-second. For optical stimulation using ChR, optical pulses with a repetition frequency from several to hundreds of hertz is often used. In contrast, optical inhibition with NpHR requires constant illumination to inhibit stochastic firing action potentials.

B. Noise Model of High Input Impedance Amplifier with Optogenetic Noise

Figure 3:
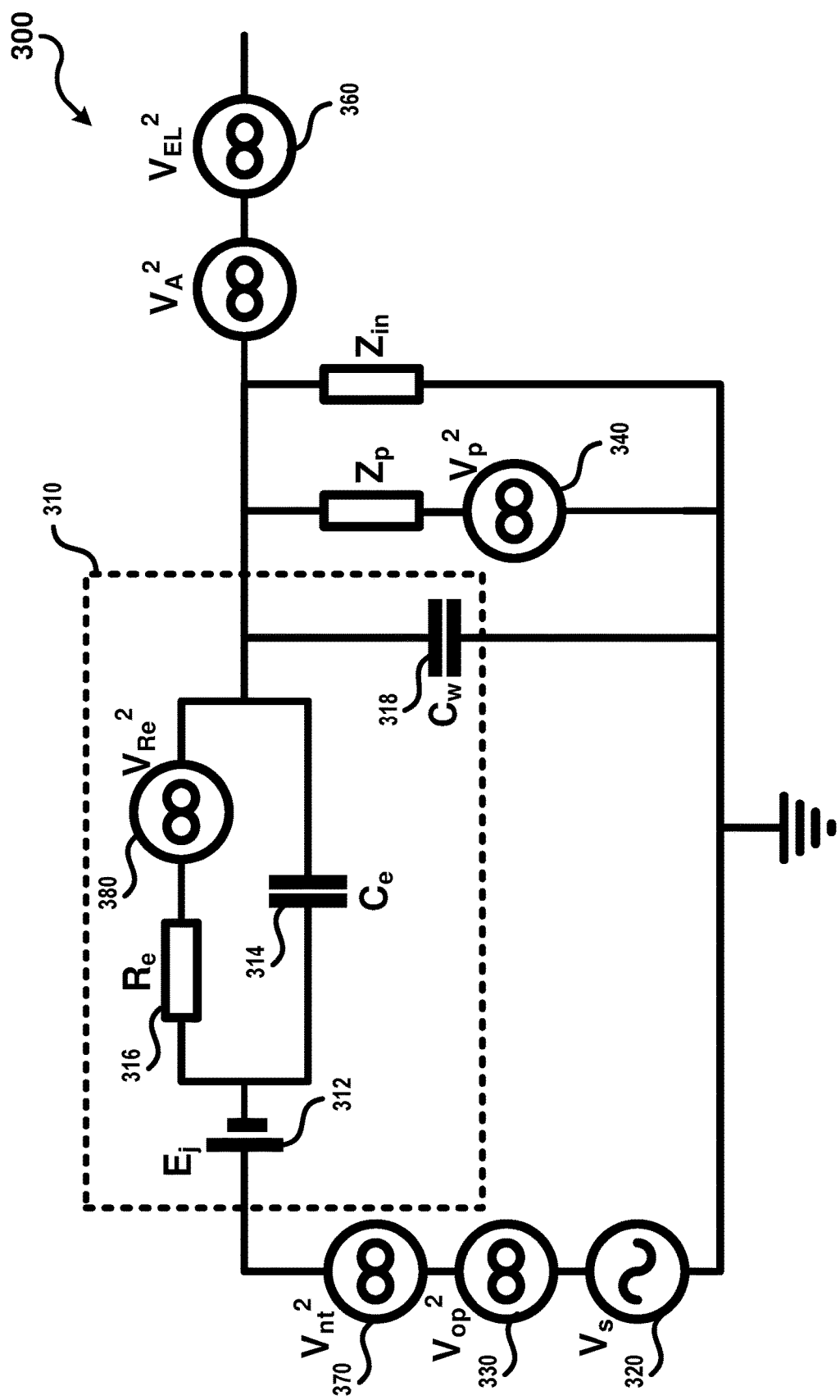
FIG. 3 represents a noise model to analyze interference of the neural amplifier in which a metal electrode was used to measure action potentials extracellularly with a high current driver for optical illumination included to perform optogenetic controls that can be used in some embodiments of the present technology.

FIG. 3 represents a noise model 300 to analyze interference of the neural amplifier in which a metal electrode was used to measure action potentials extracellularly with a high current driver for optical illumination included to perform optogenetic controls. The equivalent noise model of an electrophysiological recording amplifier can be optimized for using a high impedance metal electrode with small exposed tip. The noise model can include additional noise sources associated with high current drivers used for optogenetic control. The dotted line 310 shown in FIG. 3 surrounds the equivalent components of the metal electrode. Examples can include extracellular action potentials of the measured neuron, noise generated from the surrounding neurons, small photoelectric current generated voltage during optical illumination of the metal electrode, DC half-cell potential, leakage resistance of the electric double layer of the metal-electrolyte junction, equivalent capacitor for the electric double layer, thermal noise of insulating capacitor of the metal electrode, power-line interference, equivalent insulating resistor between the powerline and the amplifier, input impedance of the amplifier, intrinsic noise of the amplifier, fluctuation noise during optogenetic current surge.

In the noise model illustrated in FIG. 3, the tip of the metal electrode can be described by four equivalent components: 1) the DC half-cell potential Ej (312), 2) the electric double layer capacitor Ce (314), 3) the metal-electrolyte interface leakage resistor Re (316), and 4) the insulating capacitor Cw (318). Ej is the voltage potential difference between the two metal-electrolyte junctions of the metal electrode and of the reference electrode, Re (316) is the leakage resistance for charge carriers migrating across the electric double layer, and Ce (314) is the equivalent capacitor for the same electric double layer. Generally, both Re (316) and Ce (314) weakly depend on the applied signal frequency f, with a relation of $(2\pi f)^{-1/2}$. Re also weakly varies against the amplitude of the measured neural voltage Vs (320).

For simplicity, these two small effects were neglected in the discussion. The value of Re (316) is also inversely proportional to the surface area of the exposed metal tip. Many neuroscience experiments use metal electrodes with small exposed tips to minimize the detection range to the nearest neuron. The small tip results in a relatively large leakage resistance (Re~2-3 MΩ). In addition, for high impedance electrodes, Ce (314) can be approximated to be ~50 pF. The insulation layer covering the metal electrode can also form another capacitor. The insulating capacitance Cw (318) is linearly proportional to the immersion depth of the electrode and is typically approximated to be ~9.3 pF/cm for well-insulated electrodes.

In the model, Vs (320) is the voltage of extracellular action potentials generated by a neuron during measurement. This voltage typically has a range between 50 μVpp to 500 μVpp with a rise time of ~0.2 ms and a pulse duration of ~1 ms. $V_{nt}^2$ (370) accounts for all voltages arising from other neurons surrounding the measured neuron and these voltages are considered to be noise in single cell recordings. This background noise has a frequency dependence of $1/f^\alpha$ (where α=1.1 under normal conditions) and this noise is mainly dominated by frequencies below 300 Hz.

In optogenetic control, light delivered by an optical fiber is often attached adjacent to the recording metal electrode. Thus, light outputting from the optical fiber intended to illuminate the neurons will also unavoidably illuminate the metal electrode. This optical illumination on the metal electrode triggers a photoelectric effect to generate a sudden surge of small current. The voltage 330 generated by this small photoelectric current can be considered an electric artifact of the measured neuronal signal and denoted as $V_{op}^2$ (330) in the model. Fortunately, this illumination noise can easily be separated from neural action potentials since the noise aligns well with the onset of the optical illumination. Finally, the dominating noise of the entire model is the thermal noise $V_{Re}^2$ (380) generated from the leakage resistance Re (316). Due to the high value of Re (316), this noise is typically about a few tens of μVpp over the measurement bandwidth.

There are also other experimental noise sources which can play a factor in the model if not carefully eliminated. The 50/60 Hz power line interference can also be described as a noise source (340). The electrical insulation between the recording amplifier and the laboratory power line can be represented by an equivalent impedance Zp (350). Caution should be taken in the laboratory to electrically isolate the neural amplifier from the laboratory noise as much as possible (maximizing Zp). For instance; a Faraday cage can be used to shield the amplifier and the experimental setup to minimize signal contamination, $V_{BL}^2$ (360) is the additional electrical noise caused by the current fluctuation affecting the amplifier when the optogenetic current driver is operating.

Useful IC design guidelines can be drawn from the noise model. To start, several less important noise sources can be removed from the model for simpler analysis. As mentioned, careful implementation of shielding around the experimental setup can reduce power line noise $V_p^2$ (340) to a minimum. Metal electrodes with small exposed tips are often used to reduce $V_{nt}^2$ (370). Post-processing filtering and good IC design practices can be implemented to minimize $V_{op}^2$ (330) and $V_{EL}^2$ (360). Thus, the thermal noise of the electrode $V_{Rs}^2$ (380) remains as the dominant noise of the system. The SNR of the system can then be approximated to be $$SNR \approx \frac{V_s}{\sqrt{\frac{V_{Re}^2}{2} + V_A^2\left[\left(1 + \frac{C_{in}}{2C_e}\right)^2 + \left(\frac{C_{in}}{2C_e}\right)^2\right]}}$$

Two design guidelines can be subsequently drawn from the above equation: 1) the lower the input capacitance (or the higher the input impedance, where $Z_{in}=1/j2\pi f C_{in}$), the higher an SNR can be obtained, and 2) if the input capacitance $C_{in}$ is much lower than $C_e$ of the electrode, i.e.

$$\frac{C_{in}}{2C_e} \to 0,$$

the above equation can be further reduced to $$SNR \approx \frac{V_s}{\sqrt{\frac{V_{Re}^2}{2} + V_A^2}}$$

Therefore, the amplifier should have an intrinsic noise of at least lower than the half of the thermal noise $V_{Re}^2$ (380) to achieve an optimal SNR. For a metal electrode with an 3MΩ impedance, the thermal noise at room temperature (300 K) with a 5 KHz measurement bandwidth is estimated to be $\sqrt{V_{Re}^2} \approx 18.2$ $\mu V_{rms}$. Therefore, the amplifier intrinsic noise should be designed to be lower than half of this level.

II. IC DESIGN AND EXPERIMENTAL SETUP

A. IC Design

Figure 4A:
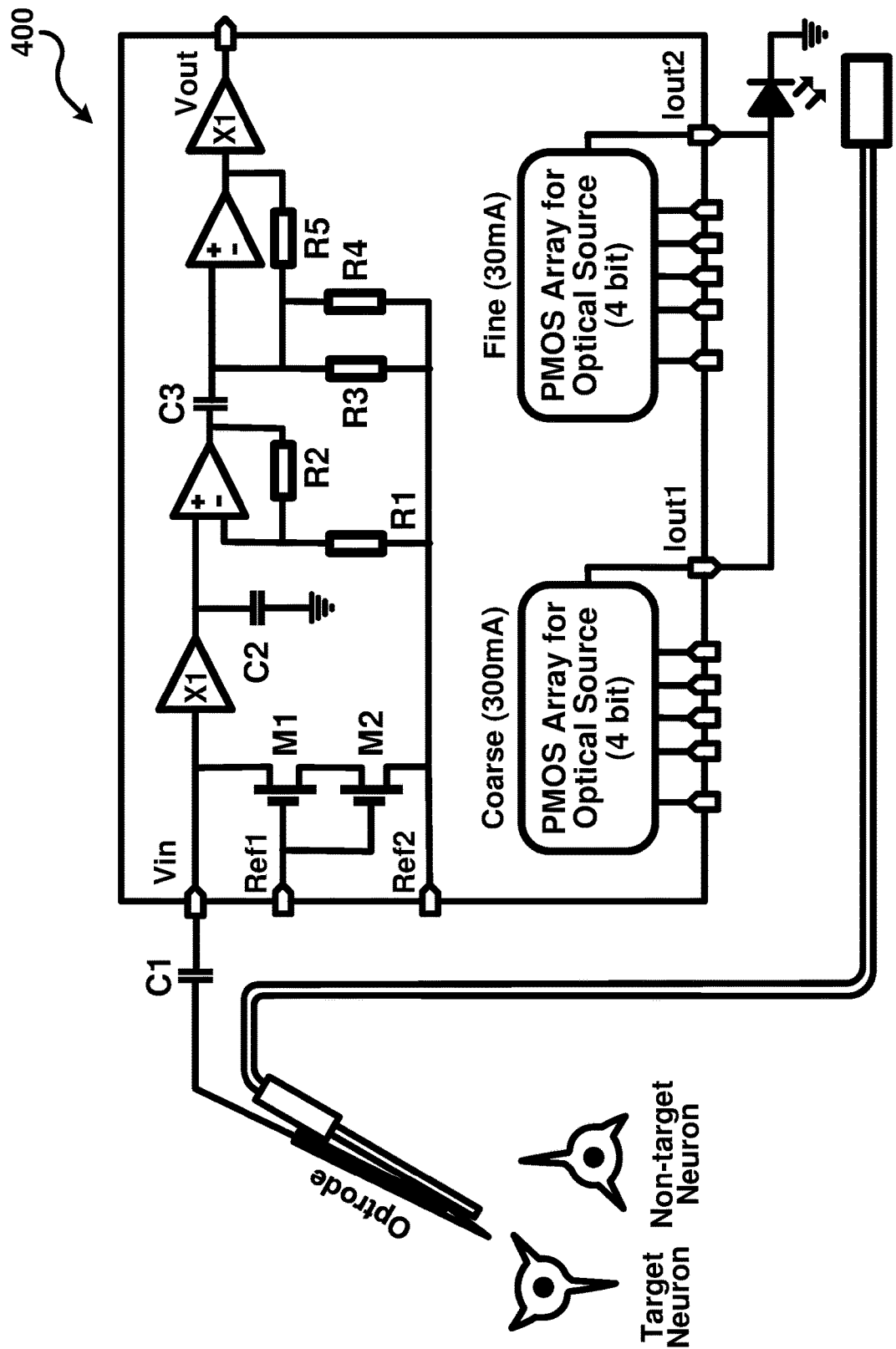
FIGS. 4A-4C illustrate various schematic diagrams of ICs that can be utilized in various embodiments that integrate a high input impedance neural amplifier optimized of using a high impedance metal electrode for single neuron electrophysiology recording and two adjustable high current laser/LED driver for optogenetic stimulation or inhibition.

FIG. 4A illustrates the schematic diagram 400 of the IC for extracellular single cell recording and simultaneous optogenetic control according to various embodiments of the present technology. In some embodiments, the IC can be designed and fabricated using the 0.18 μm CMOS processing technology of Global Foundries (Santa Clara, Calif.). Other embodiments may use different processing technologies. As described by the noise model, the input impedance of the recording amplifier should be designed to be as high as possible and also to have a low intrinsic noise to achieve a good SNR.

In conventional neural amplifier designs where high impedance electrodes were not used, a high gain CMOS amplifier serves as a first stage without optimizing the input impedance. Without a high enough input impedance of the amplifier, the high impedance of the metal electrode will share the action potential voltage with the amplifier, leading to a reduced SNR. For this reason, a unity gain buffer can be used in some embodiments as the first amplifying stage to especially optimize for a high input impedance (e.g., 9.7 pF), leaving the amplification to be handled by second and third stage amplifiers. One disadvantage of adding a unity-gain amplifier to achieve higher input impedance is that the design sacrifices some power efficiency due to the additional power needed for the first stage. However, the increase in power consumption is negligible in most optogenetic experiments since the current driver consumes a much larger current (e.g., hundreds of mA).

A capacitor C1 can be connected to two MOSFET transistors (M1 and M2), which were used as two adjustable resistors; forming a high-pass filter to reject the DC half-cell potential Ej. The filter avoids the DC half-cell potential acting as a large offset overloading the amplifiers. Ref1 is an external contact point of which the resistance values of M1 and M2 can be adjusted by supplying an external voltage to fine-tune the cut-off frequency of the low-pass filter. The second contact point Ref2 serves as a bias voltage to set the operation point of the all three amplifying stages. The second stage design was based on a low-noise and low-power operational transconductance amplifier and was used to amplify the input signal with a moderate gain. The second stage gain is adjustable by setting the ratio of the two resistors R2 and R1 and was optimally set to have a gain of 26 dB to prevent noise from surrounding neurons (Vnt) and power line interference (Vp) saturating the amplifier. These two noises were subsequently filtered before the signal entering the third amplifier by a high-pass filter formed by C3 and R3. The third amplifier was finally implemented to have an overall gain ~51.5 dB to amplify the neural signal to a voltage level of ~200 mVpp. Another unity gain buffer can be used as the final power stage to provide an output current adequate to drive an analog-to-digital converter (ADC) for signal digitization at the output.

Two programmable PMOS arrays can be used provide a combined maximum current (e.g., 330 mA) to drive the optogenetic light source. The first and second PMOS arrays can generate maximum currents (e.g., 300 mA and 30 mA, respectively). In accordance with some embodiments, each of the PMOS arrays can have a 4-bit digital input for the users to adjust the current outputs. The current resolutions for the first and the second PMOS arrays may be 18.75 mA and 1.875 mA, respectively. The first benefit of having a two-stage current control is to allow a finer current adjustment for the optical output level. The second benefit is to improve the response time of the optical output. Due to the fact that semiconductor laser diodes or LEDs have a negligible optical output before the driving current reaching a threshold, the temporal response of the optical output can be improved by using the first PMOS array to drive the light source slightly below threshold to maintain a very low optical output, and by stepping the driving current above the threshold using the second PMOS stage, such that the optical power can be rapidly increased.

Figure 4B:
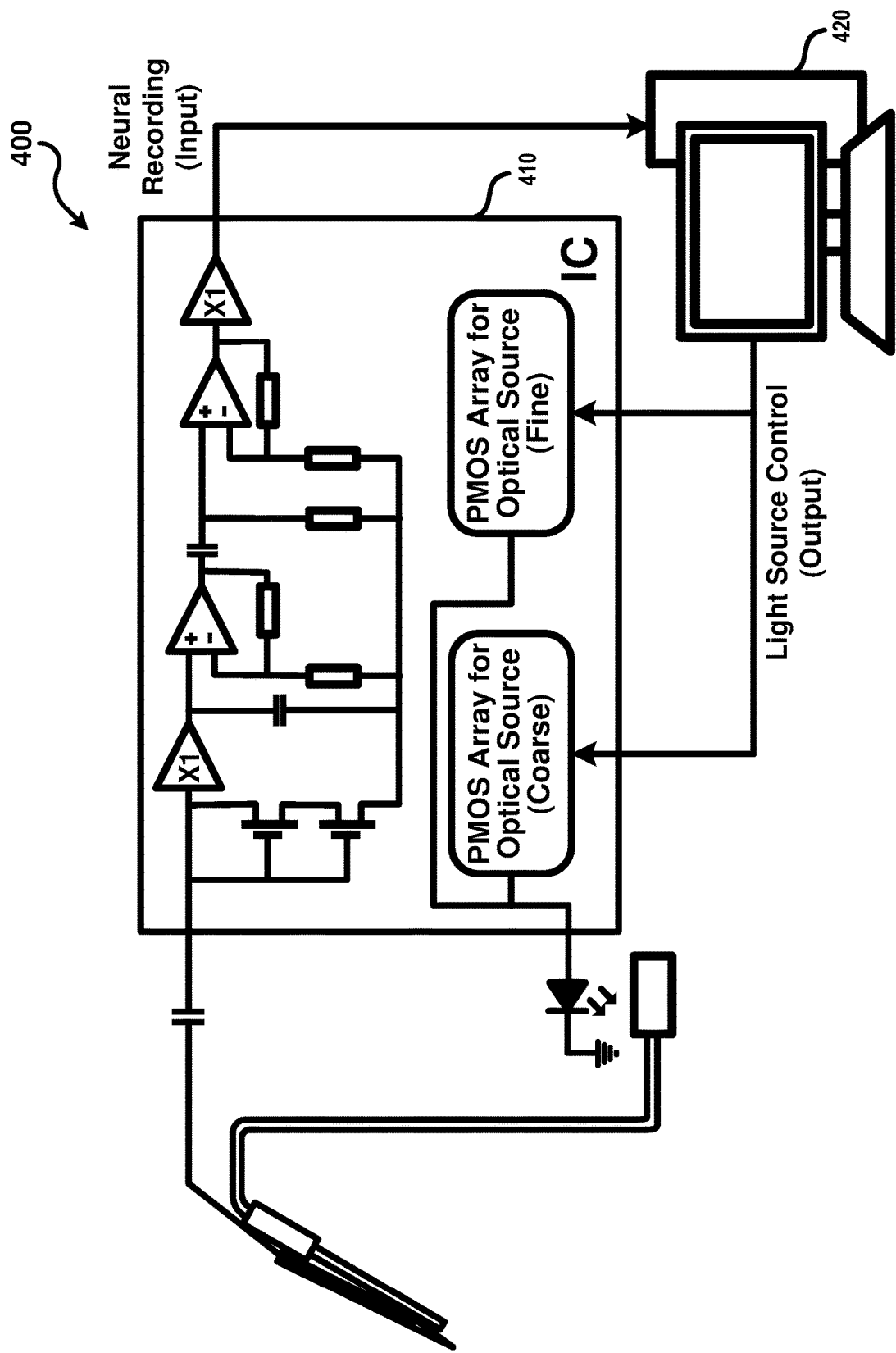

FIG. 4B illustrates some embodiments of the present technology that include IC 410 where the neural amplifier and the light source driver was integrated into a single IC. The control of IC 410 was controlled by a host computer 420 which handles the signal digitization, noise filtering, and data processing of the input neural data; and at the same time controls the operation of the light source driver for optogenetic stimulation and inhibition. As shown in FIG. 4B, the neural amplifier to record action potentials from a neural target and a high current laser/LED driver were integrated in a single monolithic IC 410. The neural data measured by the neural amplifier can be sent to a host computer 420 for signal digitization, noise filtering; and other signal processing processes that are required to allow users and/or software to analyze and interpret the recorded data. At the same time, the host computer 420 can also be used to control the high current laser/LED driver on demand for optogenetic manipulation (excitation or inhibition), either whenever the analyzed results generated from the neural recording match predetermined and preprogrammed criteria, or through direct human intervention.

Figure 4C:
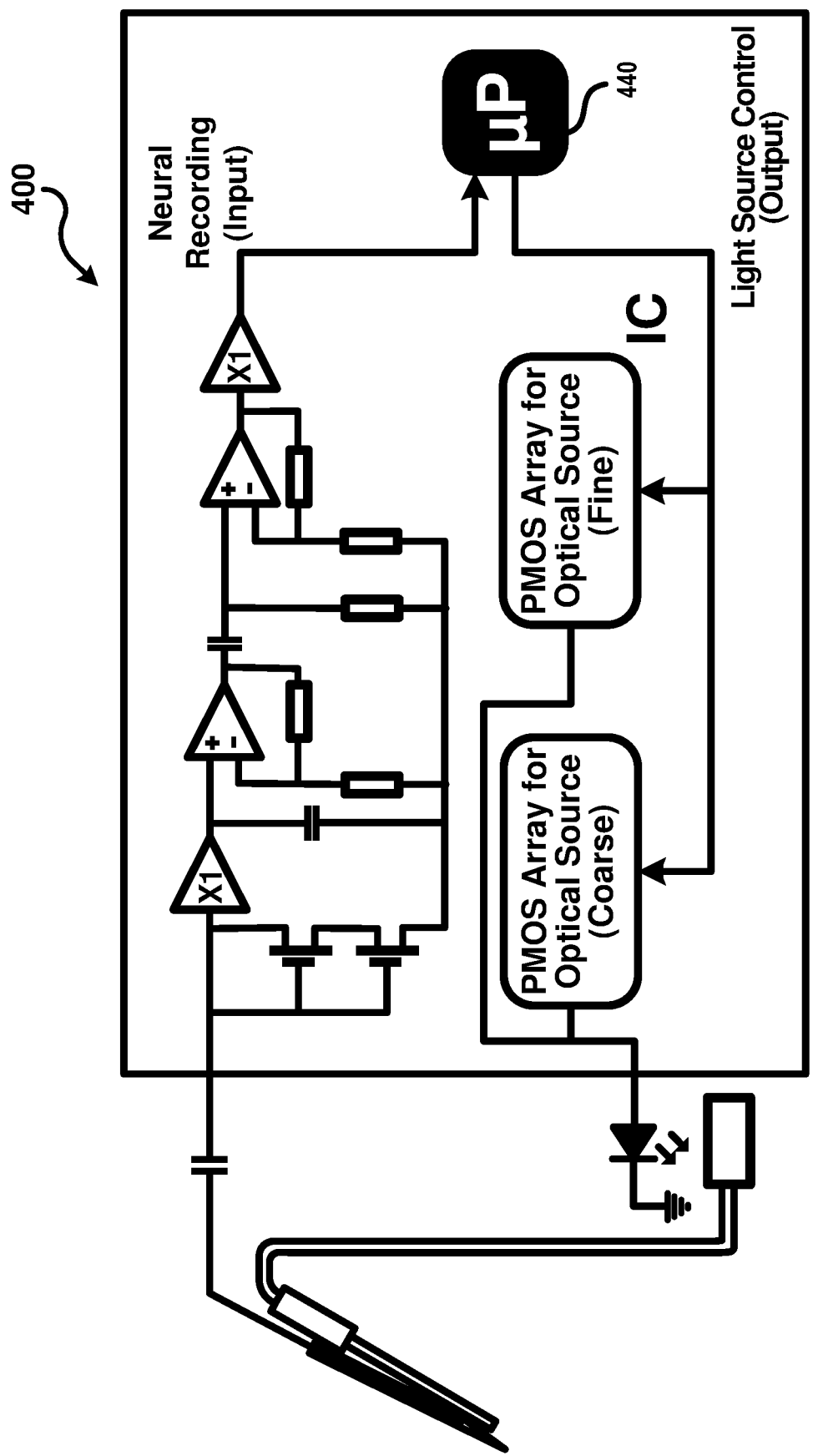

FIG. 4C illustrates other embodiments of the IC 410 where the neural amplifier and the light source driver was integrated into a single IC. In the embodiments illustrated in FIG. 4C, microprocessor technology was utilized to directly integrate a microprocessor 430 into the IC in which the microprocessor handles the signal digitization; noise filtering, and data processing of the input neural data; and at the same time controls the operation of the light source driver for optogenetic stimulation and inhibition. The integrated microprocessor 430 illustrated in FIG. 4C, can take over all the functions of the external host computer 420 shown in FIG. 4B, including signal digitization, data smoothing, signal processing and on-demand laser/LED current driver controls.

In accordance with various embodiments, some or all of the computing steps can be performed onboard the device or by an external computer. Computing steps include things such as spike sorting, recognition of firing patterns, overall levels of neural activity, or responses to specific environmental conditions. One benefit of onboard processing is the possibility to build autonomous neural prosthesis which can independently activate the optogenetic proteins when certain conditions are met. For example, epilepsy is a condition in which certain brain areas become unphysiologically active. Inappropriate neural activity starts somewhere in the brain and spreads to other areas, leading to a seizure.

Some embodiments can include an amplifier, a processor, and an optogenetic controller. Moreover, these embodiments can: 1) continuously monitor a patient's levels of neural activity (the amplifier part); and/or 2) feed that activity into the central onboard processor for analyses such as spike sorting and determination of overall firing levels. Computational rules would be applied via software that runs on the processor; such "whenever the activity levels exceed X, respond with an action;" and 3) the action would be to turn on the light via the LED controller, shining light onto the affected brain areas which then either turn on or off (because they are optogenetically manipulated)—thereby regulating brain activity until it is back to normal, avoiding the seizure.

There are other examples of medical conditions that could be treated with such a device: Parkinson's, depression, and several others. The underlying techniques used in various embodiments can includes the following: measure neural activity->process that information and decide if it needs to be modulated->modulate with light as needed.

Figure 5:
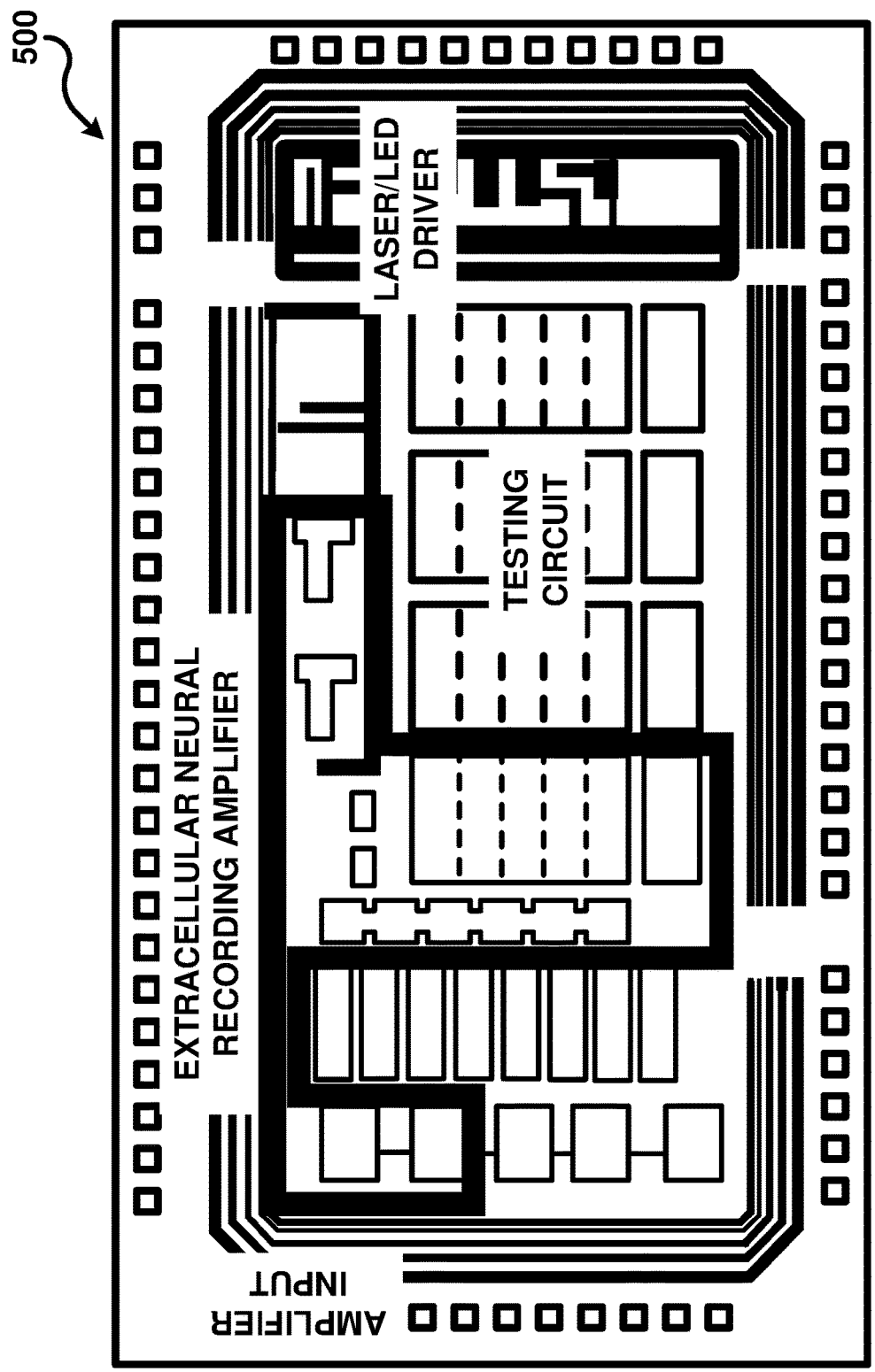
FIG. 5 is a diagram of the fabricated IC that may be used in one or more embodiments of the present technology that includes a neural amplifier and the laser/LED driver unit and additional testing circuits.

A photograph of some embodiments of the IC is shown in FIG. 5. In the embodiments illustrated in FIG. 5, the dimensions of the IC can be approximately 2.9×1.6 mm including the non-essential testing circuit. The IC chip consists of two regions—an extracellular neural recording amplifier and a programmable laser/LED driver (two PMOS units). The neural recording amplifier and the laser/LED driver were positioned opposite to each other at the two ends of the IC to minimize electrical interference to the recording amplifier when the laser/LED drivers are driving large currents.

Simulations of the amplifier performance (e.g., frequency response and input referred noise) were conducted using Cadence (e.g., an IC design software—Cadence Design Systems, San Jose Calif.) during the design phase to compare with the experimentally measured results. The frequency response of the amplifier was also experimental measured using a dynamic signal analyzer (e.g., 35670A, Agilent Technologies, Santa Clara Calif.) on the fabricated ICs.

The input impedance of some embodiments of the amplifier were measured using a 1 Vpp sinusoidal voltage with a sweeping frequency from 1 to 5000 Hz was connected to a 10 MΩ resistor and the neural amplifier in series. The 10 MΩ resistor and the input capacitor of the neural amplifier forms a low pass filter, and the frequency response of this low pass filter can be measured at the output of the unit gain stage. The 3 dB cutoff frequency of the frequency response curve was then used to calculate the input capacitance of the amplifier.

B. Optrode

Figure 6A:
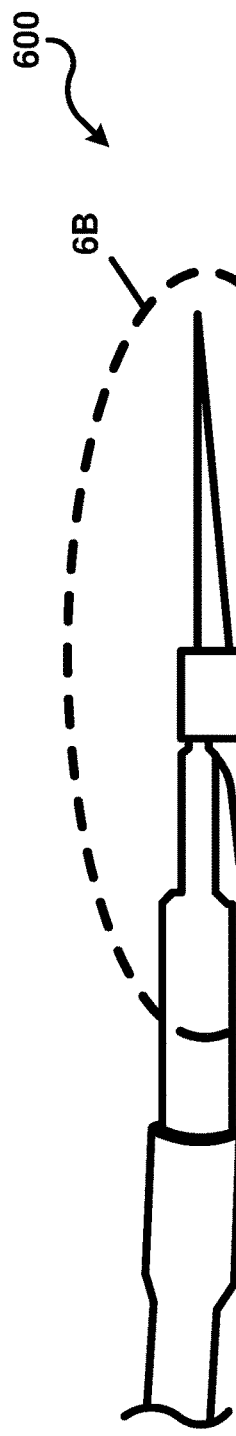
FIG. 6A is a schematic diagram of the optrode showing the high impedance metal electrode and the optical fiber for optogenetic illumination that may be used in accordance with some embodiments of the present technology.
Figure 6B:
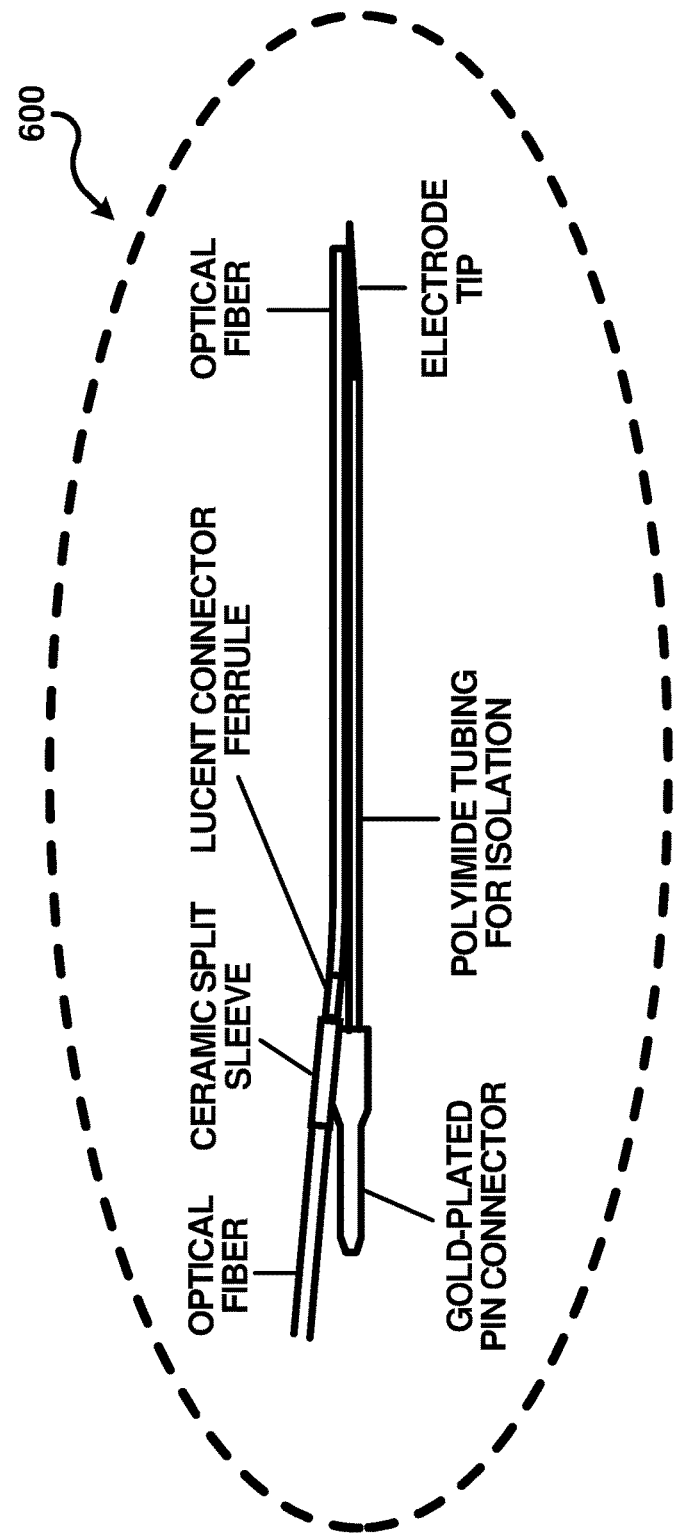
FIG. 6B illustrates additional details of the same optrode that may be used in one or more embodiments of the present technology.

An implantable "optrode" integrating both a metal electrode and an optical fiber for simultaneous electrophysiology recording and optogenetic control was designed and fabricated. The optrode can be used together with the custom IC as a complete package for animal neural experiments. A schematic diagram and the finished optrode are shown in FIGS. 6A-6B. The metal electrode (e.g., WEPT33.0B10, MicroProbes, Gaithersburg Mass.) can be made out of Tungsten and isolated by a coating of polyimide with an opening of ~5 μm at the tip. Because of the small tip opening, the impedance of the metal electrode may be high (e.g., ~3 MΩ at 1 kHz).

A core diameter multimode optical fiber (e.g., a 200 μm core diameter optical fiber, FT200EMT, Thorlabs, Newton N.J.) can be affixed (e.g., glued) to the side of the Tungsten metal electrode. The tip surface of the optical fiber was carefully polished to minimize optical loss by surface scattering. A 1.25 mm OD multimode ceramic Zirconia ferrule (e.g., Precision Fiber Products, Milpitas Calif.) may be used in some embodiments to encapsulate the fiber coupling end. A ceramic split sleeve can then be inserted to couple laser light to the optical fiber.

In addition, index matching gel (e.g., G608N3, Thorlabs, Newton N.J.) may be scribbled onto the fiber tip during the matching process to improve the coupling efficiency between the fiber and the laser. With this procedure, the optical fiber can achieve a coupling efficiency as high as 90% in some embodiments. To glue the optical fiber to the metal electrode, the metal electrode may be placed under a dissecting microscope and the optical fiber was held by a three-axis micro-manipulator for precise positioning, and the fiber tip was positioned around 100 μm above the tungsten metal electrode. This ensures the neuron under measurement was indeed illuminated by the optical radiation. UV dental cement can then be applied to secure all parts of the optrode. The overall light coupling efficiency in some embodiments can be above 80% for the final assembled optrode, and the maximum optical power achieved at the output of the fiber may be around 796 mW/mm$^2$.

C. Experimental Setup for Testing the IC

Figure 7:
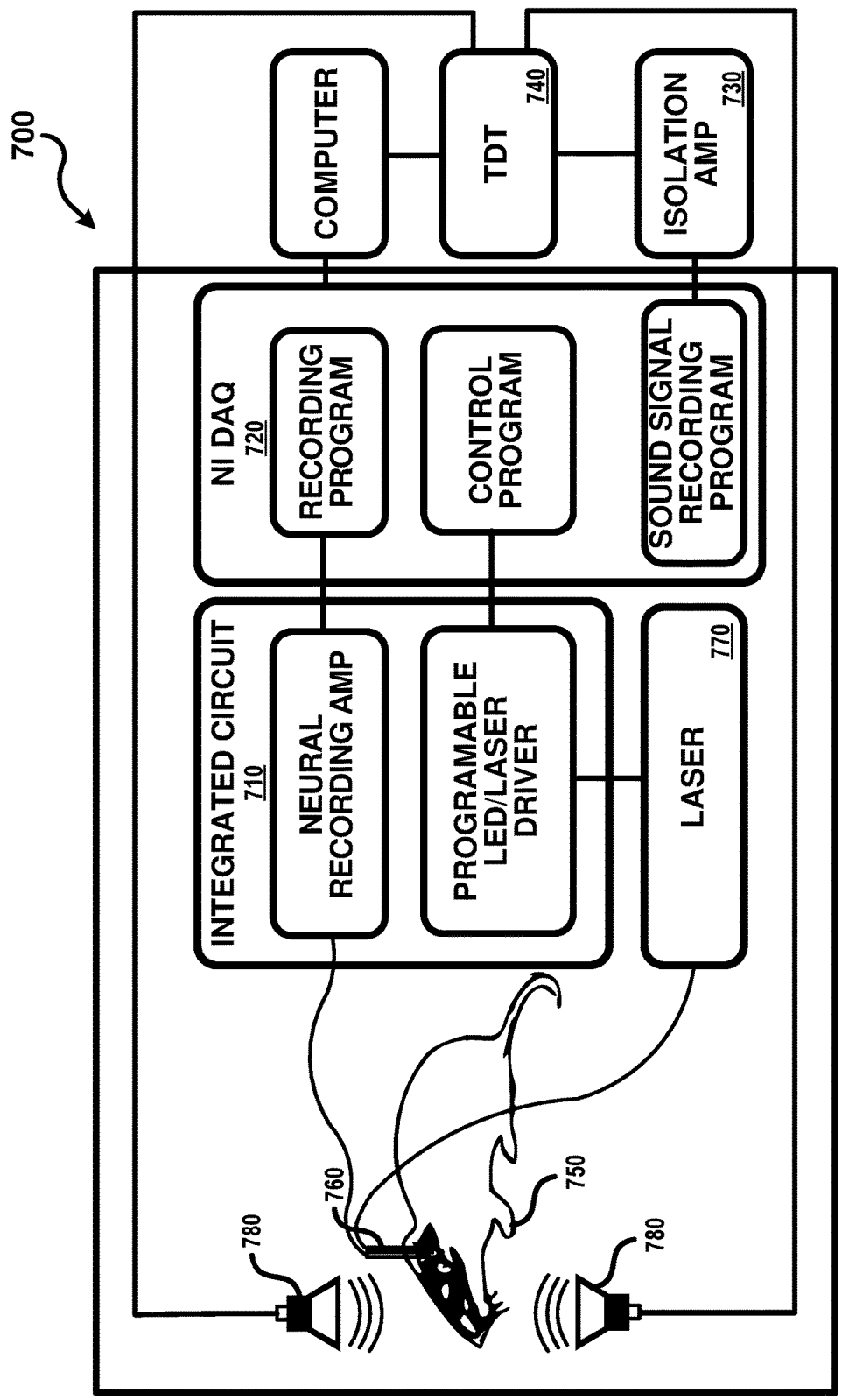
FIG. 7 illustrates an experimental setup for simultaneous optogenetic inhibition and electrophysiological recordings from the brainstem of an anesthetized gerbil according to at least one embodiment of the present technology.

To test the IC chip in simultaneous neural recording and optogenetic control, an in-vivo electrophysiology system with audio stimulation was designed and used for data collection. FIG. 7 is the block diagram 700 illustrating an example in-vivo animal auditory neuroscience setup that may be used in accordance with one or more embodiments of the present technology. As illustrated in FIG. 7, the IC 710 can be connected to a data acquisition card (e.g., NI-DAQ) 720 for signal digitization and laser power control. An isolation amplifier 730 can be used to isolate the neural amplifier from environmental noise. An audio signal processor (e.g., TDT) 740 can be used to generate a tonal signal to drive two speakers placed in the ears of the gerbil 750 for auditory stimulation of the inferior colliculus.

After the animal (e.g., gerbil) is positioned securely in the system, an optrode 760 mounted on a micro-manipulator (e.g., Inchworm controller 8200, EXFO Burleigh Products, Victor NY) can be carefully driven into the brain. The manipulator used in some embodiments may have a linear resolution of 1 μm to locate the neural target. A tungsten metal electrode can then be connected to the neural amplifier of the IC chip for signal amplification. A Faraday cage can be constructed around the experimental setup to reduce environmental interference.

To reduce interference when large currents were used to drive the two audio speakers as described below, an isolation amplifier (e.g., ISO124, Texas Instruments, Dallas Tex.) can be used to further isolate the amplifier to the subsequent electronics. The output from the isolation amplifier was then connected to a data acquisition card (e.g., NI USB-6341, National Instruments, Austin Tex.) for digitalization and the data was subsequently captured by a computer for further analysis. A Butterworth 4th order infinite-impulse-response (IIR) band-pass filter (e.g., 300 Hz-5 kHz) can be applied to the digitized signal to filter the low-frequency noise originating from the remaining 50/60 Hz power-line interference. The data acquisition card 720 may also have several digital outputs which can be connected to the laser/LED PMOS current drivers 770 to control the supplying currents for the laser to generate light for optogenetic controls. To minimize brain tissue damage due to continuous optical illumination, the laser/LED driver can be programmed to have a maximum duration of less than five seconds. The laser on and off times were also recorded together with the recorded neural voltage by a custom control software written in LabVIEW (National Instrument, Austin Tex.). Firing rates of the action potentials were calculated using a custom Python program, in which a threshold was set to reject the noise floor to identify action potentials.

Two multi-field magnetic speakers 780 (e.g., MF1, Tucker-Davis Technology, Alachua Fla.) may be placed against both ears of the gerbil 750. A single frequency tone was generated by an audio signal processor (e.g., RX6, Tucker-Davis Technologies, Alachua Fla.) and played through the two speakers.

III. ANIMAL PREPARATIONS AND STEREOTACTIC HpNR VIRAL INJECTION

A. Animal Preparations and Viral Injection

In accordance with various embodiments, animals can be anesthetized with several types of anesthesia, for example a mixture of ketamine-xylazine (e.g., 60 mg/kg-5 mg/kg), and a maintenance dose (e.g., 25 mg/kg-5 mg/kg) can be given following complete anesthesia to maintain the anesthetized state. Once the animal is properly anesthetized, the fur over the skull can be shaved off and the underlying skin sanitized with a disinfectant. Skin and muscle overlying the skull can be removed and a craniotomy was made in the skull at 1.2 mm lateral and 1.2 mm posterior of lambda using a dental drill. A screw can also be placed in the skull over the forebrain with a gold connector as a ground source. The coordinates used in some embodiments allowed access to both brain regions recorded from (inferior colliculus and brainstem).

Optogenetic NpHR virus (e.g., AAV9.h Syn.e NpHR3.0 -eYFP.WPRE.hGH) can be injected into the brain. For example, four injections of 69 nL can be made at 3.5 mm deep followed by three injections at 3.0 mm deep for a total virus infection of 483 nL using a Nanoliter injector (e.g., World Precisions Instruments, Sarasota, Fla.). The skin over the skull can then be sutured and the animal given multiple (e.g., four) buprenorphine injections (0.1 mg/kg) over 48 hours to aid in recovery and analgesia. The animal can then incubate the virus for a period of time (e.g., at least 21 days) before experimental measurements.

B. Histology to Confirm Injection and Recording Sites

The following procedure can be used in some embodiments to confirm that virus and optrode targeted the desired brain areas. After all electrophysiological and optogenetic experiments have concluded, the animal can be given an overdose of pentobarbital (0.03 mL/g) and perfused transcardially with phosphate buffer solution (PBS) and 4% Paraformaldehyde (PFA). Once perfusion has completed, the brain can be removed and placed into 4% agar. The brainstem and cerebellum can then be sliced coronally in 100 μm sections using a vibratome (e.g., Leica VT 1000s, Nussloch, Germany). The sections can then be stained with a 1:100 concentration of Neurotrace Nissl stain (e.g., ThermoFisher, Waltham Mass., 435/455 blue fluorescent Nissl stain) diluted in antibody solution (ABS). The brain slices can then be mounted on slides with Fluoromount-G (e.g., Diagnostic BioSystems, Pleasanton Calif.) and imaged with an Olympus FV1000 (Tokyo, Japan) confocal microscope using the laser lines of 405 nm and 488 nm to image the Nissl (cell body indicator) and yellow fluorescent protein (YFP), which is the fluorescent indicator for NpHR protein expression.

IV. EXPERIMENTAL RESULTS

A. Electrical Characterization of the Amplifier

Figure 8:
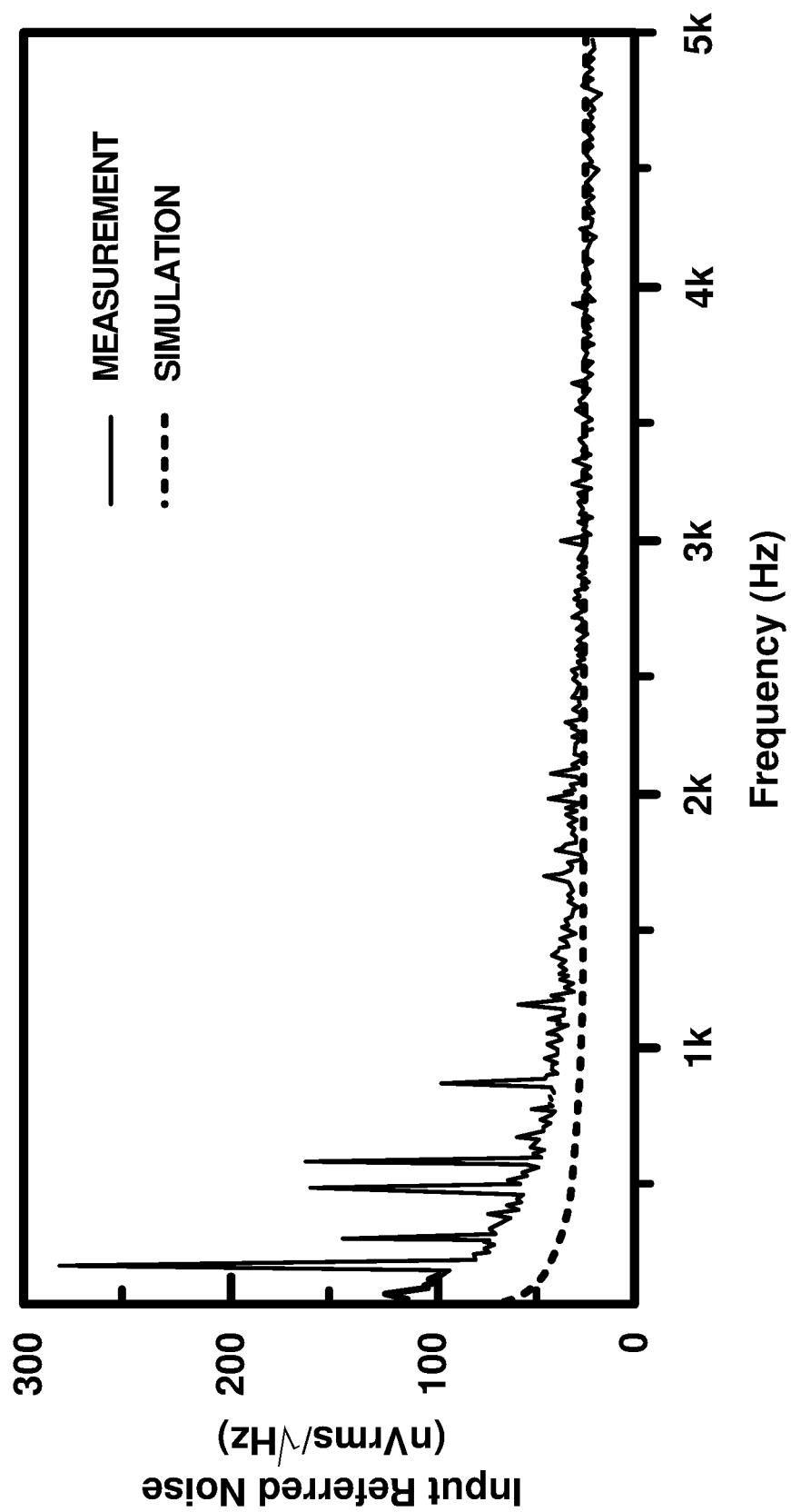
FIG. 8 is a plot of experimentally measured (solid black line) and simulated (dotted black line) input referred noise of the high input impedance neural amplifier used in some embodiments of the present technology.

Several measurements on the amplifier of the IC used in some embodiments were conducted to characterize the electric performance of the amplifier. The frequency responses of the simulated (red) and experimentally measured (black) results in both amplitude and phase are shown in FIG. 8. The amplifier gain of the measured embodiments was ~51.5 dB in the pass-band and the 3-dB bandwidth of the amplifier was from 114 Hz to 14.62 kHz. The gain of ~51.5 dB selected in the design phase of some embodiments was chosen to be large enough to measure small neural signals.

Figure 9:
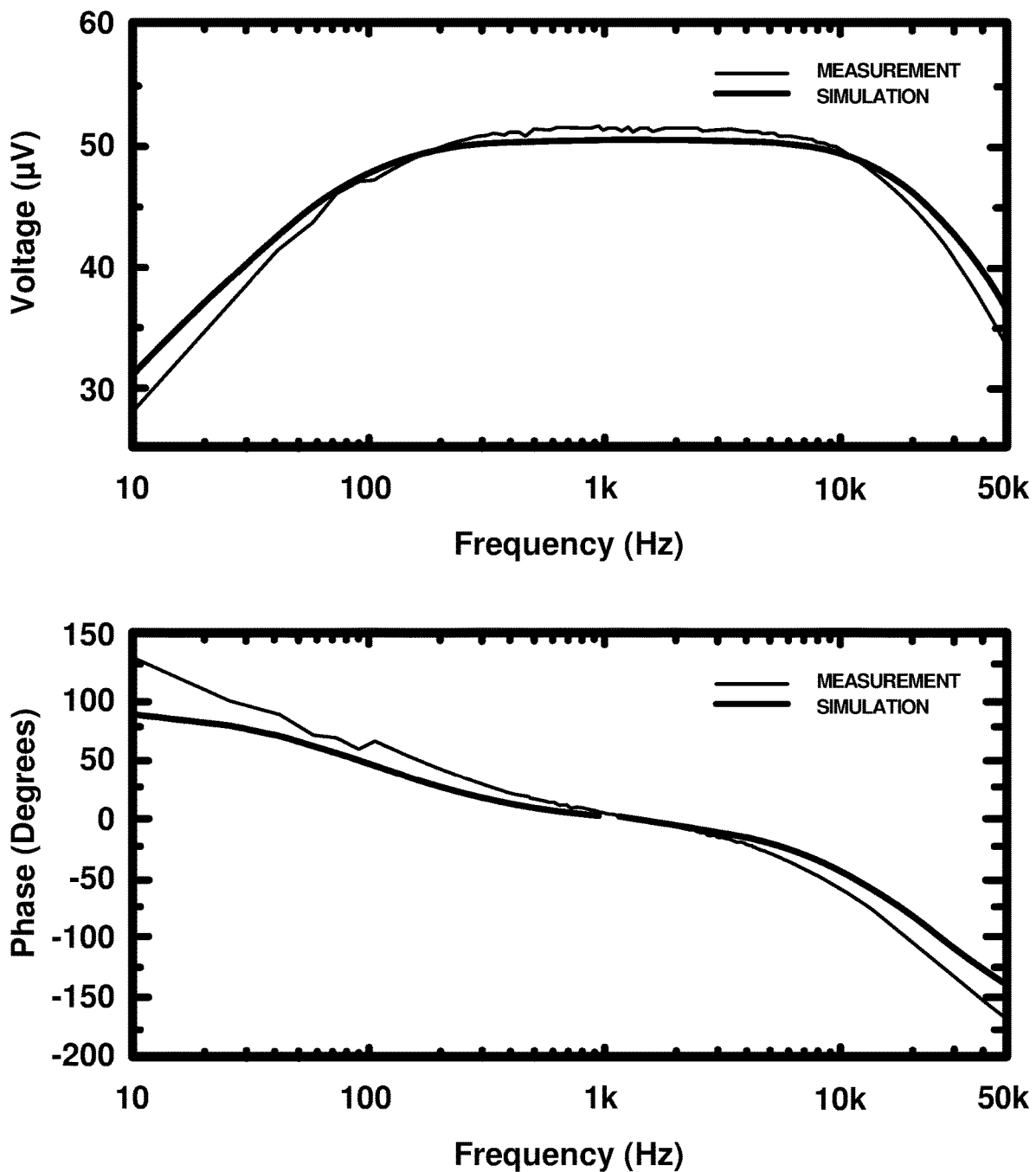
FIG. 9 are plots of experimentally measured (thin black line) and simulated (thick black line) frequency response of the gain (top panel) and phase (bottom panel) of the high input impedance neural amplifier.

Typically, extracellular neural spikes are in the order of hundreds of micro-volts peak-to-peak, depending on the location of the electrode relative to the neuron, as well as the type of neuron. The design criteria can be set to amplify neural voltages as low as 50 μVpp. A 51.5 dB gain will allow amplification of the 50 μVpp to 18.35 mVpp, which is ~60 times bigger than the binning resolution (0.3 mV) of a typical 16-bit analog-to-digital converter. As shown in FIG. 9, there is only a small discrepancy between the experimentally measured and the simulated frequency responses and this discrepancy is likely due to the expected manufacturing variations. To ensure that the manufacturing variations will not turn into performance instability, Monte Carlo simulations can be performed during a design phase to vary all the design parameters to ensure these small changes in the manufacturing process do not alter the overall performance of the amplifier.

The experimentally measured and the simulated input referred noises of the neural amplifier are shown in FIG. 9. The noise can be integrated between 300 to 5000 Hz, which covers the main frequencies of action potentials, for both simulated and experimentally measured noise were found to be 3.56 μVrms and 4.57 μVrms, respectively. The measured noise is 28% higher than the simulated noise and this difference is caused by the higher estimated resistances of the two input transistors M1 and M2 in the simulation. At this noise level, a minimum signal-to-noise ratio (SNR) of 2 can still be achieved for a 50 μVpp neural spike. The input capacitance of the amplifier was measured to be 9.7 pF.

Figure 10A:
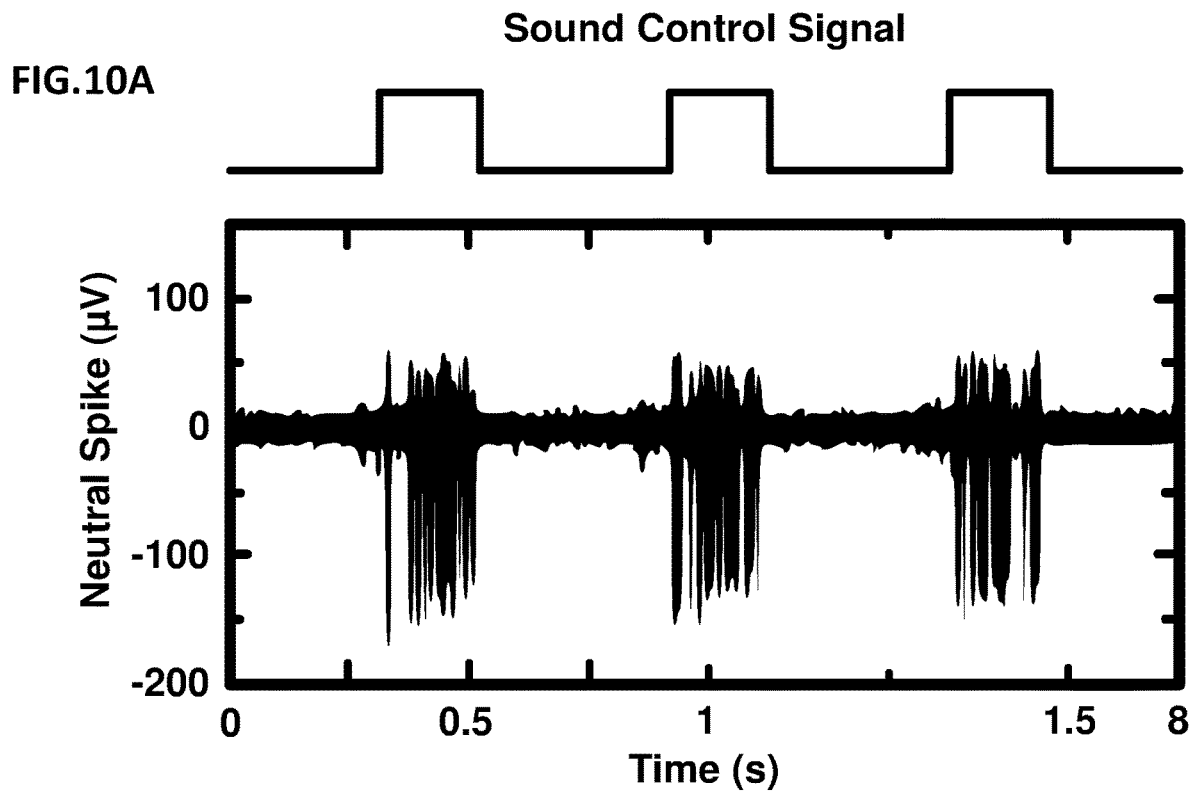
FIG. 10A shows a train of neural spikes (action potentials) recorded in-vivo from the inferior colliculus of an anesthetized gerbil using the high input impedance amplifier.
Figure 10B:
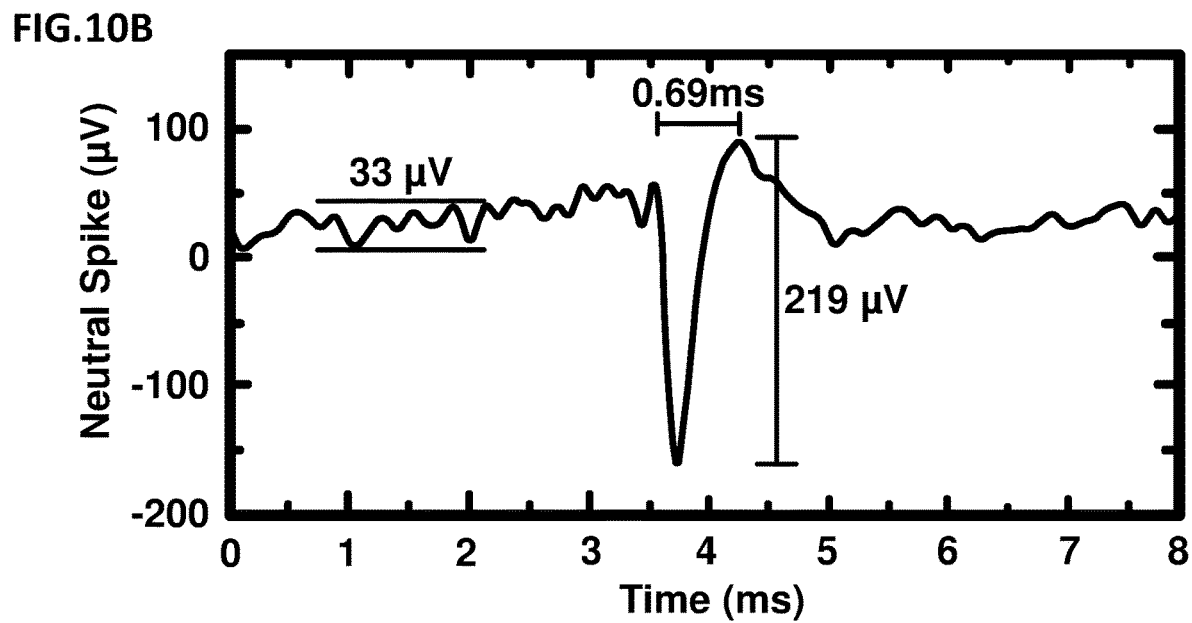
FIG. 10B show a zoom-in view of one of the neural spikes of FIG. 10A showing the measured peak-to-peak amplitude (219 µV), the pulse duration (0.69 ms) and the peak-to-peak noise level (33 µVpp)

B. Animal Testing of Single Cell Extracellular Recording and Optogenetic Inhibition To test the performance of the high input impedance neural amplifier under experimental conditions, in-vivo extracellular neural measurements were performed to record action potentials of an anesthetized gerbil. FIG. 10A plots a train of extracellularly recorded action potentials that was obtained when the electrode was placed in the inferior colliculus, an auditory signal processing brain area. Tones with a sound frequency of 4520 Hz and an ON duration of 200 ms and an OFF duration of 300 ms were presented to the ears of the gerbil via earphones. Since the inferior colliculus is part of the auditory signal processing circuit in the brain, neurons within the inferior colliculus sensitive to the sound frequency played to the ears will only fire action potentials when the sound stimulus is played. The recordings of neural activity shown in FIG. 10A reflect the occurrence of the neural spikes that correlated well with the sound stimulation. Neural spiking (measured spiking rate=61.7 Hz) only occurred during the epoch when the sound stimulus was played. FIG. 10B shows a zoomed in plot of a typical extracellular action potential measured in this experiment. The action potential has a 219 μVpp amplitude and a 0.69 ms duration. The background noise during the non-firing period was estimated to be 33 μVpp. Thus, the SNR of the measured neural spike is ~6.6, which is sufficient for in-vivo neural experiments.

Figure 11:
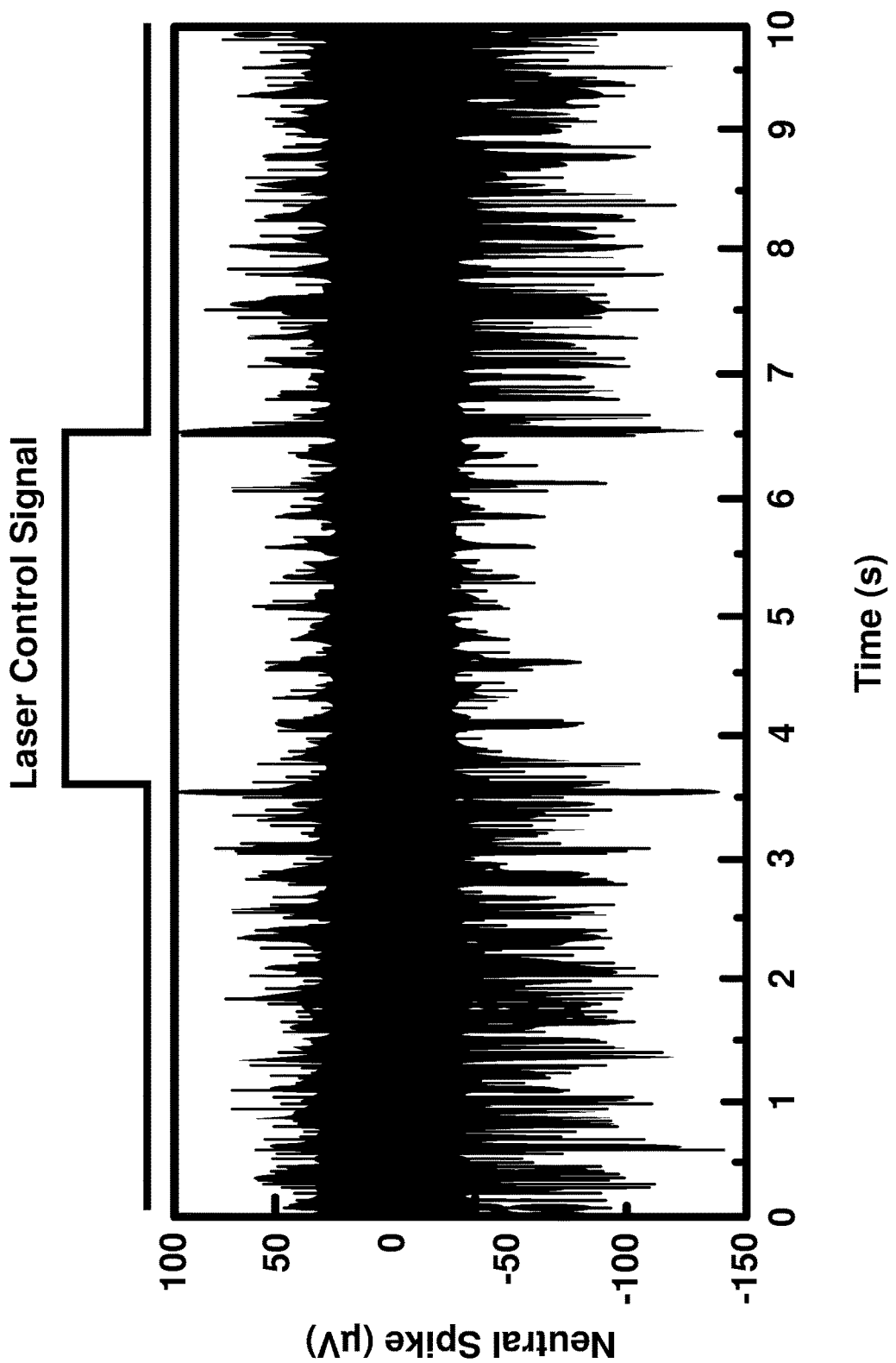
FIG. 11 illustrates the optogenetic inhibition of spontaneous action potentials in the 5th nerve of the brainstem during optical illumination of an anesthetized gerbil, using some embodiments of the IC.

In accordance with various embodiments, the IC can be simultaneously recording extracellular action potentials and at the same time delivering light to the optrode and thereby manipulating neural activity with optogenetics. This has been demonstrated by inhibiting action potentials in neurons of the fifth nerve in the brainstem. In this experiment, the brain stem of the gerbil was injected with NpHR virus, and the animal recovered from the surgery and incubate the virus for several weeks. An optrode was later positioned in the same area for optogenetic manipulation. The animal was anesthetized, and neural firing was confirmed through the output of the IC. Then optical illuminations of 3 second durations were delivered through the optical fiber of the optrode to the brainstem to activate optogenetic proteins and thereby inhibit action potential firing. FIG. 11 shows a 10 second recording of neural responses in the brainstem recording site, with a three second "laser on" silencing epoch. The amplitude and firing rate of neural spiking were observed to be significantly reduced during the laser illumination epoch, and action potential firing was recovered after optical illumination was ceased.

From the raw recording trace shown in FIG. 11, action potentials fired by a single neuron were extracted with a custom python software. Spontaneous action potential firing was significantly reduced during the three second epoch of optical illumination (between 3.5 to 6.5 second).

Figure 12:
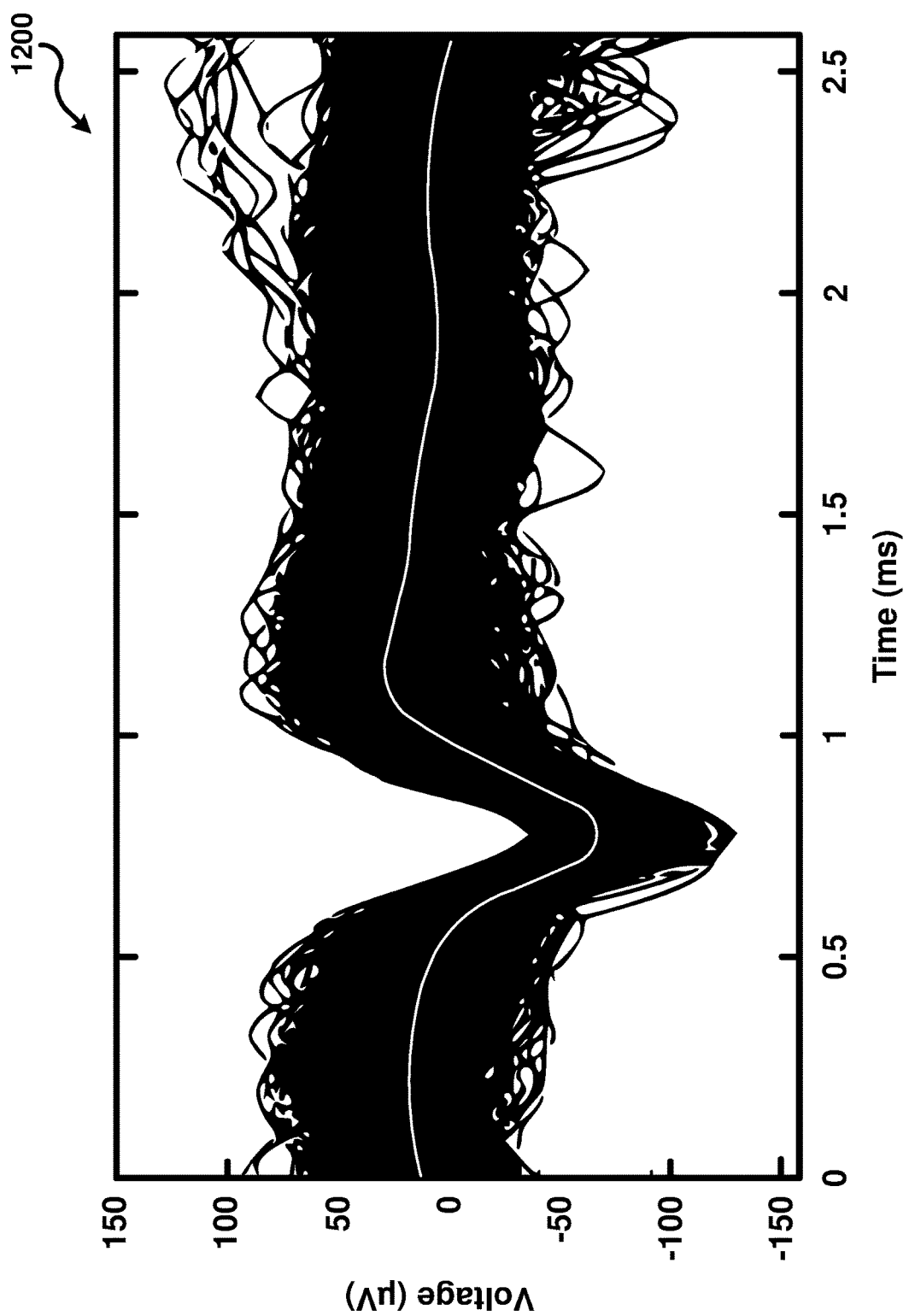
FIG. 12 is a plot showing all of the 2098 recorded spikes from FIG. 11 temporally aligned by their minimum.

FIG. 12 shows 2098 spikes fired by a single unit that was isolated from the recording trace, stacked on top of each other. The average wave form is plotted in white. All spikes have a very similar shape, which follows a typical extracellularly recorded action potential. This indicates that all the recorded action potentials originated from the same neuron. The 10 second recording with intermittent light stimulation protocol was repeated nine times and all nine trials showed similar silencing and recovering responses during and after optical illumination. The similar shape of the spikes indicates that the recorded spikes were originated from the same neuron.

Figure 13A:
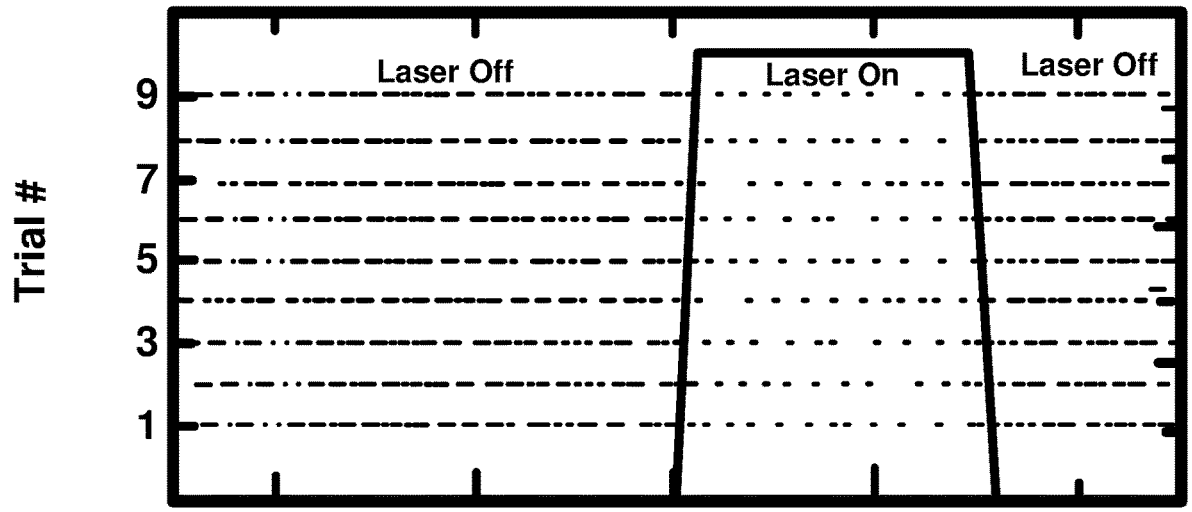
FIG. 13A is a raster plot showing the temporal locations of action potential firing over nine trials testing optogenetic inhibition using an embodiment of the present technology.
Figure 13B:
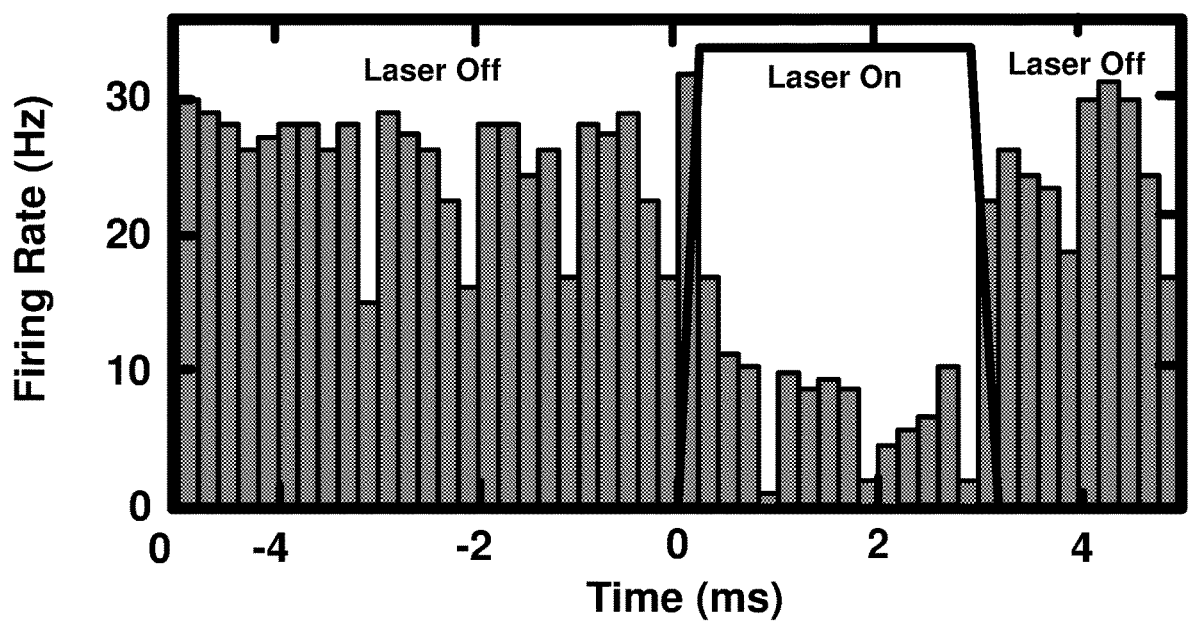
FIG. 13B illustrates the calculated average firing rate showing significant reduction of the firing rate during optical illumination.

FIG. 13A is a raster plot showing action potentials firing during the 10 second recording period for all 9 trials, and t=0 and t=3 s were aligned to the time when the laser is turned on and off respectively. FIG. 13B is the calculated average firing rate per 100 ms time bin. Before the optical illumination at t<0, the average firing rate was calculated to be 25.4 Hz. After optical illumination to inhibit the neuronal firing, the average firing rate dropped to 15.6 Hz in the first second and was stable at 7.5 Hz between 1<t<3 s; thus, the inhibition rate is 3.4. After the optical illumination stopped after t>3 s, the firing rate recovered to 24.8 Hz immediately. All nine trials showed the same inhibitory response of action potentials, as represented by the raster plot in FIG. 13A.

C. Histology Confirmed the Anatomical Location of the Recording Site

After conclusion of the electrophysiological and optogenetic experiments, each gerbil was sacrificed and transcardially perfused with paraformaldehyde. The brain was extracted and sliced with a vibratome. The brain slices containing the inferior colliculus and brainstem were imaged under a confocal microscope to confirm the optogenetic expression and the optrode placement. A viral expression in the recording site shows there is high NpHR expression near the recording site as indicated by yellow fluorescence. This indicates that the action potential inhibition was likely caused by the NpHR. The recording site for this experiment was confirmed with the help of a gerbil brain atlas to be the fifth nerve of the brainstem.

V. REAL-TIME NEURAL SPIKE SORTING SYSTEM BASED ON TEMPLATE MATCHING

Recent technical advancements allow precise recording and control of neural circuits simultaneously. In order to achieve closed-loop neural control, a rapid spike sorting system is needed for processing recorded neural spikes. Various embodiments of the present technology utilize a rapid spike sorting system based on template matching. In accordance with some embodiments, cluster templates may be first generated by a host computer using off-linespike sorting algorithm (k-mean, expectation maximization, super-paramagnetic clustering, and the like) and subsequently transferred to a FPGA or an ASIC for rapid sorting through template matching. Two (or more) different matching techniques (e.g., Euclidian distance and Correlational matching) may be user selectable for optimal sorting results.

High sorting accuracies may be achieved in some embodiments for both template-matching methods but Correlational matching can better handle spikes with non-Gaussian spike distribution. A low system latency of less than 2 ms and a maximum spike sorting rate of 941 spikes/second have been achieved with some embodiments of the system. The system was characterized using a publicly available artificial data set and were also confirmed with pre-recorded neural spikes from an anesthetized Mongolian gerbil. The rapid sorting capability of the system allows immediate firing rate calculations that are critical for closed-loop neural system control for neuroscience studies or neural disorder treatments.

A. Introduction

Recording action potentials from firing neurons gives neuroscientists the ability to study neuronal circuits inside a brain with single cell accuracy. Generally, action potentials are recorded with a metal electrode implanted or inserted into the brain of an animal or a human patient. In vivo, it is very challenging to place the electrode into the intracellular space of a neuron (intracellular or patch recording) due to pulsation and movement of brain tissue. Therefore, the metal electrodes are typically placed within the extracellular space between neurons to capture neural spikes extracellularly.

In this extracellular configuration, neural spikes generated from several adjacent neurons are often captured by the metal electrode at the same time, making it challenging to determine the activity patterns of single neurons included in these clusters. These multi-cell recordings are especially common when signals are measured from brain areas densely packed with neurons. For this reason, mathematical algorithms are often used post-experimentally to separate the neural spikes and assign them to different cluster groups, also known as spike sorting algorithms. The underlying principle for spike sorting relies on the fact that neuronal spikes originating from different neurons will have different temporal profiles (different shapes), which depend on the impedances of the extracellular fluid between the neurons and the electrode, as well as the cell membrane area from which the ionic currents can reach the metal electrode.

Conventional spike sorting algorithms are typically performed by a computer after the entire recording session has finished (off-line). In many cases, this type of off-line or post-processing approach is not an issue for experiments in which the main interest is to decrypt the functions of the neuronal circuits. Thus, many state-of-the-art spike sorting algorithms were developed under the assumption that longer computational times within a reasonable limit (several minutes) are acceptable. However, such an approach is not suitable for experiments that require rapid responses, as in scenarios of "closed-loop" neuronal control for behaving animals or neural disorder treatments. In closed-loop neural control, rapid computational results and responses are required (several milliseconds) to determine a response (output) based on the recording (input). This "closed-loop" approach is particularly important for experiments involving light-sensitive opsins, or optogenetic proteins, to intervene in neural circuits by optical illumination. This new biochemical technique opens up a new opportunity to manipulate neuronal circuits based on a certain behavioral response or certain physiological characteristics of the brain.

To record neural activity while simultaneously controlling it with light, various embodiments provide for a monolithic IC that integrates a low-noise high input impedance neural amplifier and a high current power source for both neural recording and optogenetic manipulation. This device allows researchers to record and to manipulate neuronal circuits with a single IC. However, the IC does not include a processing unit to analyze data on the fly, Instead, some embodiments include a real-time spike sorting system using the field programmable gate array (FPGA) technology assisted by a host computer, Various embodiments of the FPGA have the capability to perform real-time spike sorting by matching cluster templates pre-calculated by a host computer. For example, the host computer can calculate these cluster templates using a spike sorting algorithm (e.g., superparamagnetic clustering) that is well accepted in the neuroscience community. Neural spikes are recorded during a training session, and templates are transferred to the FPGA module for subsequent real-time spike sorting through matching the spikes to these templates.

There has been a sustained effort to develop real-time spike sorting systems. Early attempts of neural recording were capable of recording from multiple neurons and an efficient compression circuitry was implemented to allow transmitting a large amount of recorded data out of the IC for further analysis. Despite the effort, no spike sorting routine was implemented. Some traditional systems implemented a 128 channel neural recording IC with feature extraction to simplify the massive amount of collected data and to allow transmitting through wireless communication. Real-time spike sorting using a high-performance computer system, and neural spikes pre-recorded from human medial temporal lobe were sorted using their software algorithm with satisfactory results.

Traditional FPGA systems in which a spike sorting algorithm was implemented had a worst-case latency of 11 ms and were based on an approach in which the spike sorting algorithms were directly integrated into an IC at the hardware level. These approaches, however, have drawbacks, including that the sorting algorithms were somewhat simplified, and in turn, the sorting accuracy was compromised to some degree. In contrast, some embodiments of the present technology avoid these drawback using cluster templates that are pre-calculated using a more robust spike sorting algorithm by a host computer. This host computer uses data obtained from a short training period and the cluster templates are subsequently transferred to the hardware for rapid sorting.

Some embodiments use a real-time spike sorting system that uses a host computer to generate cluster templates through a parameter-free spike sorting algorithm and a FPGA module to sort neural spikes in real-time through template matching. The maximum spike sorting rate of the FPGA module is 941 spikes/second which is several times higher than the typical firing rates of neurons, allowing effectively clustering of neural spikes without loss of accuracy. Various embodiments have a latency of processing a spike that is less than 2 ms. The sorting rate and the system latency in some embodiments are approaching the theoretical limits set by the natural spike width of an action potential (~1 ms). In addition, some embodiments of the FPGA can also handle a maximum of eight neuronal clusters which exceeds the number of neurons a mid to high impedance metal electrode can simultaneously record.

The FPGA module, according to various embodiments, can implement all the necessary processing sub-units at the hardware level and does not rely on the assistance of the host computer once the cluster templates are transferred. One of two template matching methods—Euclidean distance (ED) and correlational matching (CM)—can be selected by users to sort neural spikes based on the type of noise—for optimal sorting accuracy. Rigorous testing has been performed and determined that ED can yield slightly better sorting accuracy when the spikes are contaminated by Gaussian noise. CM, on the other hand, can better handle spike amplitude fluctuations caused by the metal electrode slowing drifting away from its initial implanted position within the brain. This electrode drifting scenario is a common problem for long-term (minutes to hours) behavioral neuroscience studies performed on awake animals.

B. Method

Figure 14:
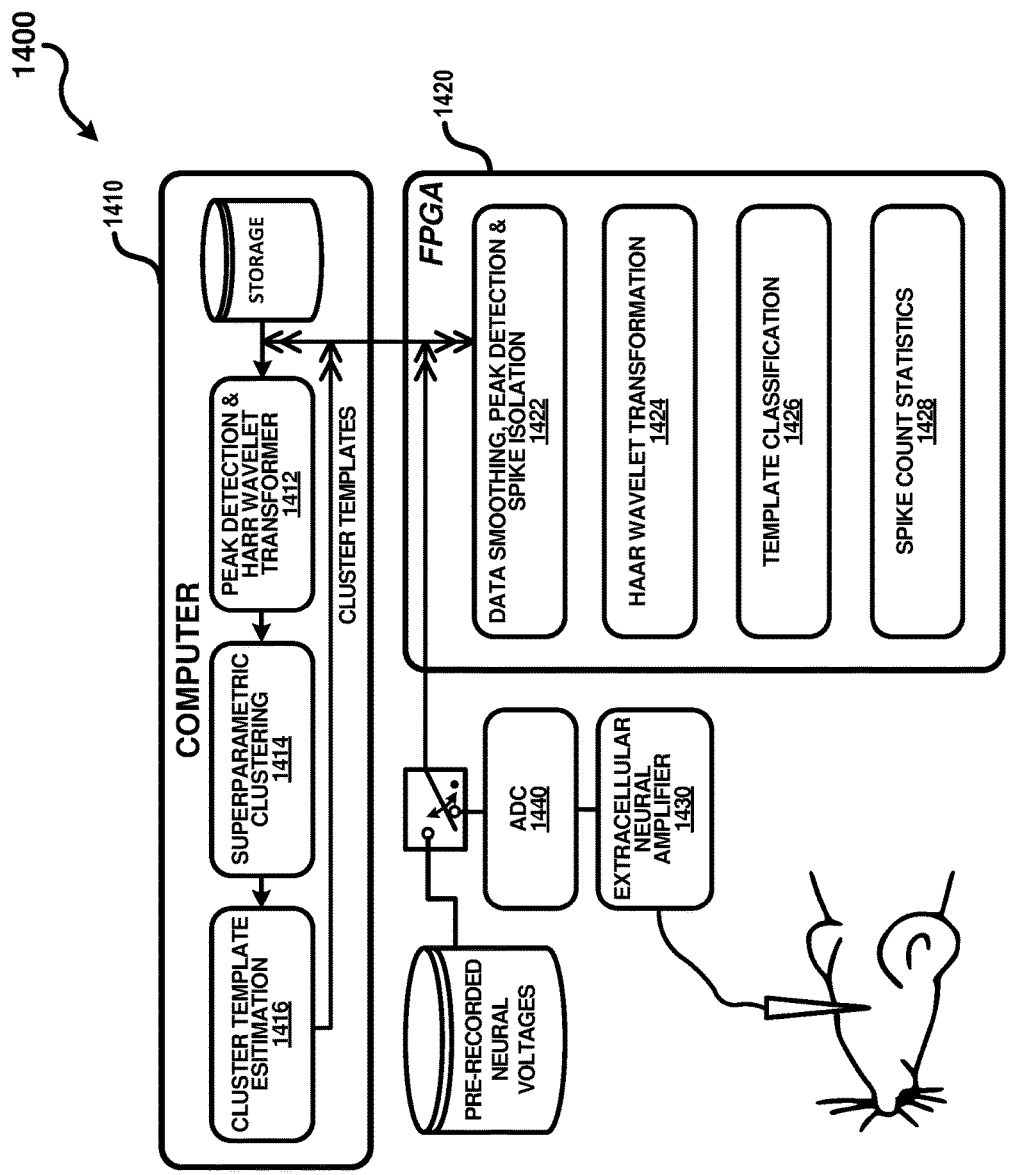
FIG. 14 is a schematic diagram illustrating the signaling between the host computer and the FPGA module that may be present in some embodiments of the present technology.

Some embodiments include two major hardware components—a host computer running a spike sorting program to generate cluster templates, and a FPGA module for rapid spike sorting through hardware template matching, either using ED or CM. FIG. 14 is a schematic diagram 1400 illustrating the signaling between the host computer 1410 and the FPGA module 1420. The internal processing sub-units of both the host computer 1410 and the FPGA 1420 are also depicted in the figure.

Since the host computer 1410 has a powerful microprocessor, it is capable of handling sophisticated spike sorting algorithms, allowing more accurate estimation of cluster templates. Some embodiments use a Superparamagnetic Clustering (SPC) as a spike sorting algorithm to generate the cluster templates with the advantage that the algorithm does not require any user inputs. Particularly, SPC does not require an estimation of the number of spike clusters contained in the digitized neural voltage as in the case of other simpler cluster algorithms. This allows full automation in the template generation process with no user input. The host computer software contains three major processing subunits—1) spike detection and feature extraction, 2) SPC calculation, and 3) cluster template estimation—with the goal of generating accurate cluster templates for the FPGA.

As illustrated in FIG. 14, extracellular neural spikes can be directly recorded by a neural amplifier 1430 with an analog-to-digital converter (ADC) 1440, or simulated from pre-recorded neural voltages for testing. The host computer 1410 can include three sub-processing units—1) peak detection and Harr wavelet transformation unit 1412, 2) super-paramagnetic cluster algorithm 1414, and 3) cluster template estimation unit 1416. The FPGA module 1420 also contains four sub-processing units—1) data smoothing, peak detection & spike isolation unit 1422, 2) Harr wavelet transformation 1424, 3) template classification unit 1426, and 4) spike count statistical unit 1428. The classification method (e.g., Euclidian distance (ED) or correlational matching (CM)) may be selectable by the users in the template classification unit of the FPGA in some embodiments.

Spike Detection and Feature Extraction

After the digitized neural voltage x[n] is captured by the FPGA and subsequently transferred to the host computer 1410 (e.g., through the USB-UART port), the host computer software can determine the peak locations of the neural spikes from x[n]. Several methods, including amplitude thresholding, nonlinear energy operator, and stationary wavelet transform, may be used by other research groups to perform spike detection. Some embodiments may use nonlinear energy operator (NEO), also known as Teager Energy Operator (TEO), as a peak detection algorithm because of its robustness in dealing with signal fluctuations contaminated by noise and other discontinuities. The NEO energy $x_{NEO}[n]$ can be calculated from the digitized neural voltage x[n] based on the equation below.

$$x_{NEO}[n] = x[n]^2 - x[n+1] \cdot x[n-1] \quad (1)$$

A threshold voltage $x_p$ can be used to compare with to identify neural peaks. The threshold voltage $x_p$ can be automatically estimated by using three times of the standard deviation of the NEO energy $x_{NEO}[n]$ or simply specified by the users, After a peak is identified, neural spikes can be cut from the neural voltage x[n] into a 32-byte data array $x^i[n]$ where i is the sequential index of the neural spikes, and n is now limited to a value between 0 and 31 for each of the spikes.

Feature extraction can also be performed to condense the temporal profiles of neural spikes into characteristic features to help improve clustering accuracy between the spike groups. Principal component analysis (PCA) and wavelet transformation (WT) are the two major methods used in feature extraction in some embodiments. Comparatively, PCA calculates the features based on maximizing the variance of the signals in the phase space, whereas WT calculates the correlation of the signals against a selected set of wavelets. Generally speaking, for neural spike sorting, wavelet transformation produces better results because the optimal variance directions in PCA are not necessarily the best directions for spike separation. For this reason, WT may be selected as the feature extraction method in some embodiments, in addition to choosing Haar wavelets for the wavelet transformation due to the robustness in transforming neural spikes. The mathematical expressions of the Haar wavelets are listed in Eqns. (2) and (3), where m is the scale level; k is the time translation; fs is the sampling frequency; l is the temporal window width; and φ(t) is the Haar mother wavelet, $$\Psi_{m,k}(t) = 2^{\frac{m}{2}} \varphi\left(t - \frac{kl}{2^{m-1} f_s}\right) \quad (2)$$

$$\varphi(t) = \begin{cases} 1 & 0 \le t < \frac{l}{2f_s} \\ -1 & \frac{l}{2f_s} \le t < \frac{l}{f_s} \\ 0 & \text{otherwise} \end{cases} \quad (3)$$

Superparamagnetic Clustering (SPC) Algorithm for Generating Cluster Templates

After feature extraction, a spike sorting algorithm can be employed to generate cluster templates. Mathematically speaking, spike sorting algorithms are unsupervised clustering methods to group neural spikes with similar features to the same cluster group. Thus, many standard unsupervised clustering techniques, including K-means, K-means++ and Fuzzy c-means, have been tried for spike sorting. However, all of these clustering techniques require prior knowledge of the cluster number (the value K), which is often unknown during neuroscience experiments. The cluster number also depends on many experimental parameters, such as the relative position of the measuring metal electrode to the neurons. For this reason, nonparametric clustering algorithms are better choices in general.

SPC is an unsupervised spike sorting method that is well accepted by the neuroscience community for off-line spike sorting studies. This technique has been demonstrated to improve the sorting accuracy comparing to other parametric sorting methods. The SPC algorithm was inspired by statistical mechanics in which phase transitions of micro magnetic domains occur as the ambient temperature increases in a magnet. Based on this idea, the SPC algorithm can randomly assign a neural spike with a spin value, and the spin values of all the spikes constitute a spin state of the entire recording. The total internal energy of a spin state can be calculated by summing the mutual interaction energies of all the spin states in which the mutual interaction energy is not zero and depends on the mutual distance only when the two spikes have different spin values.

The probability distribution of the total internal energy of the spin state follows the Boltzmann distribution, as in a real physical magnetic system. Monte-Carlo techniques (e.g., Swenden-Wang or Wolff techniques) can be used to select a limited number of spin states to approximate the total probably distributions, and in turn, these spin states are used to estimate the clustering of micro-domains within the system. The micro-domains tend to align uniformly in low temperature but align randomly in high temperature. This is due to the fact that lower energy states are more favorable in low temperature (ferromagnetic) and higher energy states are allowed as the temperature rises (paramagnetic). SPC occurs at a transition temperature between the ferromagnetic and paramagnetic states in which nearby neural spikes are clustered into a micro-domain. After finding the cluster templates with SPC, the spike templates can be transferred to the FPGA module through the USB-UART port.

II.2 A FPGA Module for Real-Time Spike Sorting

After receiving the template clusters from the host computer, the incoming spikes can be sorted by the FPGA in real-time through template matching. Users can specify the choice method (e.g., CM or ED) for the matching based on the electrophysiology recording conditions during the experiment. The FPGA has several hardware sub-units that are illustrated in 14.

The FPGA module can be implemented, for example, using an Arty FPGA development board (Xilinx; San Jose Calif.) on which it contains an Artix-7 35T FPGA and a 12-bit analog-to-digital converter (ADC) sampling at $f_s=24$ kHz. Data communication between the host computer and the FPGA was through a 12 MBPS USB-UART board (FT4232H; Future Technology Devices International, Glasgow, Scotland). The FPGA can be programmed using Verilog hardware description language (HDL) with the Vivado Design Suite (Xilinx; San Jose, Calif.).

Figure 15:
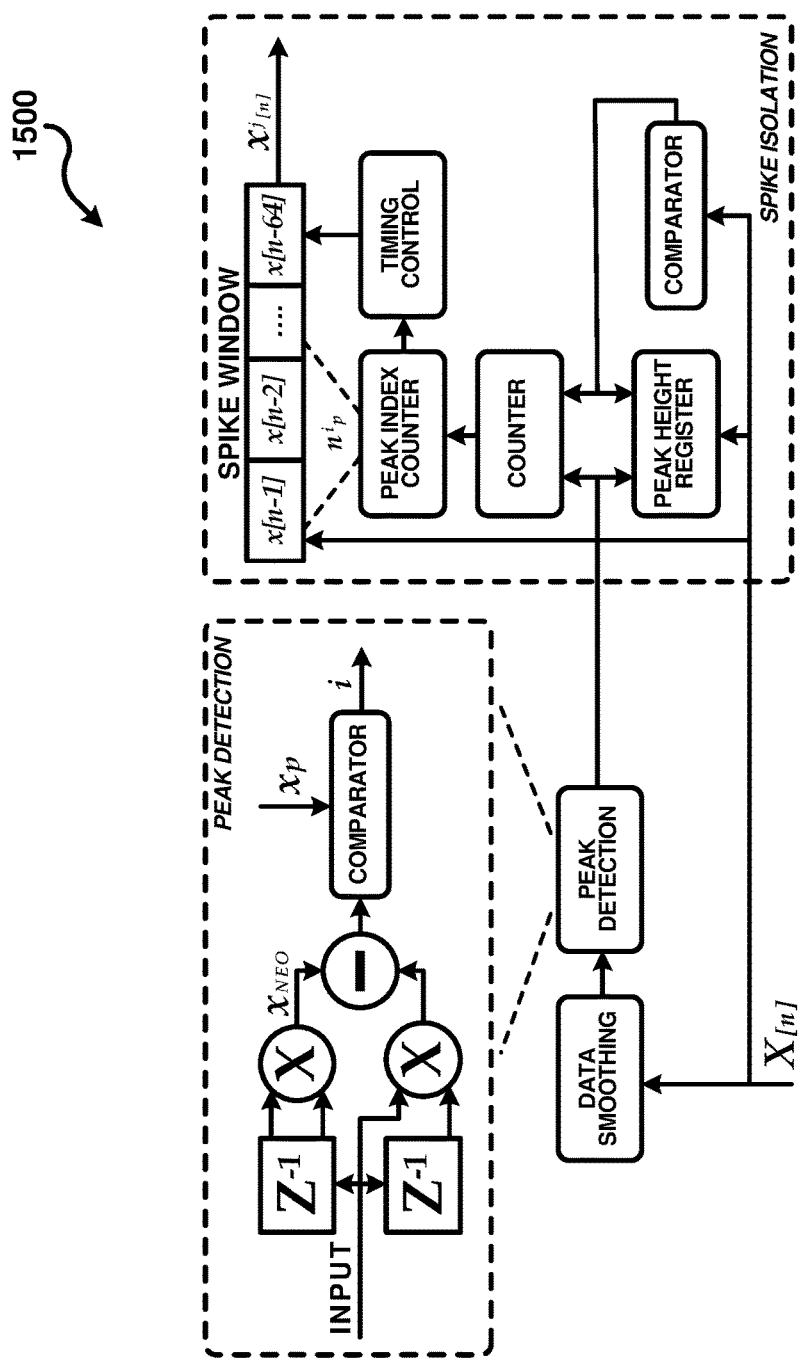
FIG. 15 illustrates a block diagram of a hardware implementation of the spike detection and isolation that may be used in accordance with various embodiments of the present technology.

FIG. 15 illustrates a block diagram 1500 of a hardware implementation of the spike detection and isolation that may be used in accordance with various embodiments of the present technology. The embodiments illustrated in FIG. 15, illustrate a smoothing filter (e.g., 8-bytes) to remove high frequency noise from the input neuron signal, followed by a NEO energy calculator and a threshold comparator to locate the data around the peak of a neural spike. A 64-byte FIFO was used to temporally store the digitized data stream. A peak index counter and a peak height register worked synergistically to determine the peak index to isolate the neural spike from the continuous data stream into a 32-byte data array.

Data Smoothing, Peak Detection, and Spike Isolation

The digitized neural voltage $x[n]$ can be fed into the FPGA module with a sampling rate of $f_s=24$ kHz. An average moving filter (n=8) can be used to smoothen $x[n]$ removing any undesired high frequency noise. The user can disable the average moving filter if the spike signal already has a high SNR and no filtering is required.

The smoothened neural voltage $x[n]$ can then be sent to a 64-byte FIFO memory for storage and later spike isolation. $x[n]$ can also converted to its NEO energy $x_{NEO}[n]$. If $x_{NEO}[n]$ is larger than the threshold $x_p$, it indicated that a neural spike was detected. The peak index counter cam, in turn, be reset to zero and the NEO energy $x_{NEO}[n]$ can be transferred to a peak height comparator to find the peak maximum index.

If the next incoming NEO energy $x_{NEO}[n+1]$ is larger than the stored $x_{NEO}[n]$, indicating that the neural voltage was on a rising edge, the peak index counter can be advanced by 1 and the value in the peak height register can be replaced by the new $x_{NEO}[n+1]$. Until the incoming NEO energy became less than the stored value, the peak of the neural spike can be identified, and the value of the peak height counter can be the peak index for the peak. This triggers the FIFO to output a 32-byte array $x^i[n]$ using the peak index $n_p^i$ for alignment, or mathematically the process can be written as the following equation to express the spike isolation process, where $$x^i[n]=\Sigma_{k=0}^{14}x[n_p^i-15+k]*\delta[n-k]+x[n_p^i]*\delta[n-15]+\Sigma_{k=1}^{16}x[n_p^i+k]*\delta[n-15-k] \text{ for } n=0\ldots31 \quad (4)$$

The neural spike $x^i[n]$ can then be transferred to the Haar wavelet transformer for feature extraction.

Haar Wavelet Transformation

A Haar wavelet transformer can be used to convert the spike data $x^i[n]$ to its corresponding wavelet features $w^i[n]$. A four-level Haar wavelet transformer can be implemented in the FPGA and the transformations of each of the four levels can be calculated by the following equations, $$\text{Level 1} \quad d_1^i[n] = \frac{x^i[2n] - x^i[2n+1]}{\sqrt{2}} \quad (5)$$

$$a_1^i[n] = \frac{x^i[2n] + x^i[2n+1]}{\sqrt{2}}$$

for $n = 0 \ldots 15$ $$\text{Level 2} \quad d_2^i[n] = \frac{a_1^i[2n] - a_1^i[2n+1]}{\sqrt{2}} \quad (6)$$

$$a_2^i[n] = \frac{a_1^i[2n] + a_1^i[2n+1]}{\sqrt{2}}$$

for $n = 0 \ldots 7$ $$\text{Level 3} \quad d_3^i[n] = \frac{a_2^i[2n] - a_2^i[2n+1]}{\sqrt{2}} \quad (7)$$

$$a_3^i[n] = \frac{a_2^i[2n] + a_2^i[2n+1]}{\sqrt{2}}$$

for $n = 0 \ldots 3$ $$\text{Level 4} \quad d_4^i[n] = \frac{a_3^i[2n] - a_3^i[2n+1]}{\sqrt{2}} \quad (8)$$

$$a_4^i[n] = \frac{a_3^i[2n] + a_3^i[2n+1]}{\sqrt{2}}$$

for $n = 0 \ldots 1$

The 32-byte Haar wavelet feature array $\vec{w}^i$ can be finally constructed using the four level outputs in which $\vec{w}^i = \{a_4^i, d_4^i, d_3^i, d_2^i, d_1^i\}$.

Template Classifier Selectable for Euclidean Distance (ED) or Correlational Matching (CM)

In accordance with various embodiments, the template classifier implemented in the FPGA module can be selectable to perform either ED or CM template matching. In some implementations, ED can give slightly higher sorting accuracy for Gaussian noise contamination, but CM can perform significantly better for neural spikes with non-Gaussian fluctuation. This non-Gaussian fluctuation can be caused by an electrode drifting over the course of a behavioral experiment for example. Thus, the capability in various embodiments to allow users to specify which comparison technique to use not only gives users flexibility but may also yield better sorting accuracy.

Euclidean Distance Classifier

The ED classifier implemented in some embodiments of the FPGA can include a simply calculated Euclidean distance between the spike feature $\vec{w}^i$ to the eight cluster templates $\vec{w}_t^a$. The equation for the ED of the cluster templates $\vec{w}_t^a$ is $$d_a^i = \sqrt{\Sigma_{n=0}^{31}[w^i[n]]^2 - (\vec{w}_t^a[n])^2} \quad (9)$$

In some FPGA implementations comparing two ED values, a square operator $(d_a^r)^2$ can be implemented instead of a square root operator, which is significantly more complex to construct at the hardware level.

Correlational Matching Classifier

A CM classifier can also implemented in the FPGA. The CM classifier can be designed to handle up to eight cluster templates, and any unused correlator can be switched off if desired to save operational energy. Pearson's correlation coefficient $\rho_a^i$ between the feature $\vec{w}^i$ of spike with the cluster template $\vec{w}_t^a$ (a=1 ... 8) is defined as $$\rho_a^i = \frac{\vec{w}^i * \vec{w}_t^a}{\sqrt{(\vec{w}^i * \vec{w}^i)(\vec{w}_t^a * \vec{w}_t^a)}} \quad (10)$$

where $$\vec{w}^i * \vec{w}_t^a = \frac{1}{32}\sum_{n=0}^{31}(w^i[n] - \overline{w}^i)(w_t^a[n] - \overline{w}_t^a) \quad (11)$$

$$\vec{w}^i * \vec{w}^i = \frac{1}{32}\sum_{n=0}^{31}(w^i[n] - \overline{w}^i)(w^i[n] - \overline{w}^i) \quad (12)$$

$$\vec{w}_t^a * \vec{w}_t^a = \frac{1}{32}\sum_{n=0}^{31}(w_t^a[n] - \overline{w}_t^a[n])(w_t^a[n] - \overline{w}_t^a) \quad (13)$$

$$\overline{w}^i = \frac{1}{32}\sum_{n=0}^{31}w^i[n] \text{ and } \overline{w}_t^a = \frac{1}{32}\sum_{n=0}^{31}w_t^a[n]$$

are the averages of the wavelet feature of the spike $\vec{w}^i$ and of the cluster template $\vec{w}_t^a$ respectively.

Figure 16A:
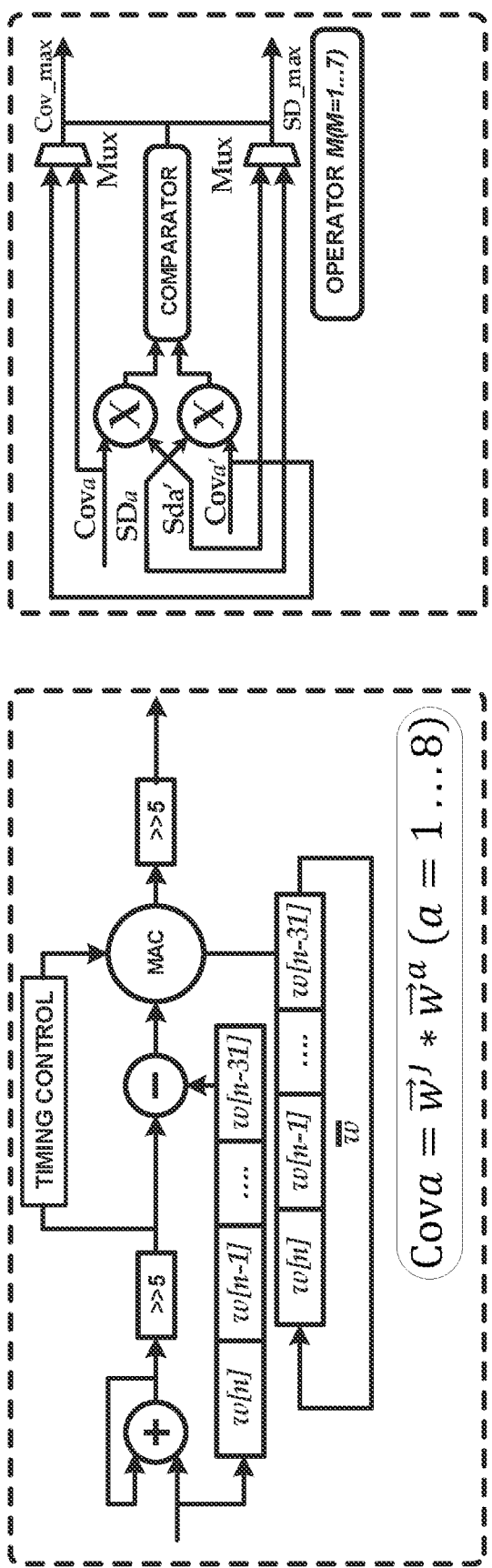
FIGS. 16A-16B illustrates a hardware implementation of the CM and ED classifiers that may be used in various embodiments of the present technology.
Figure 16B:
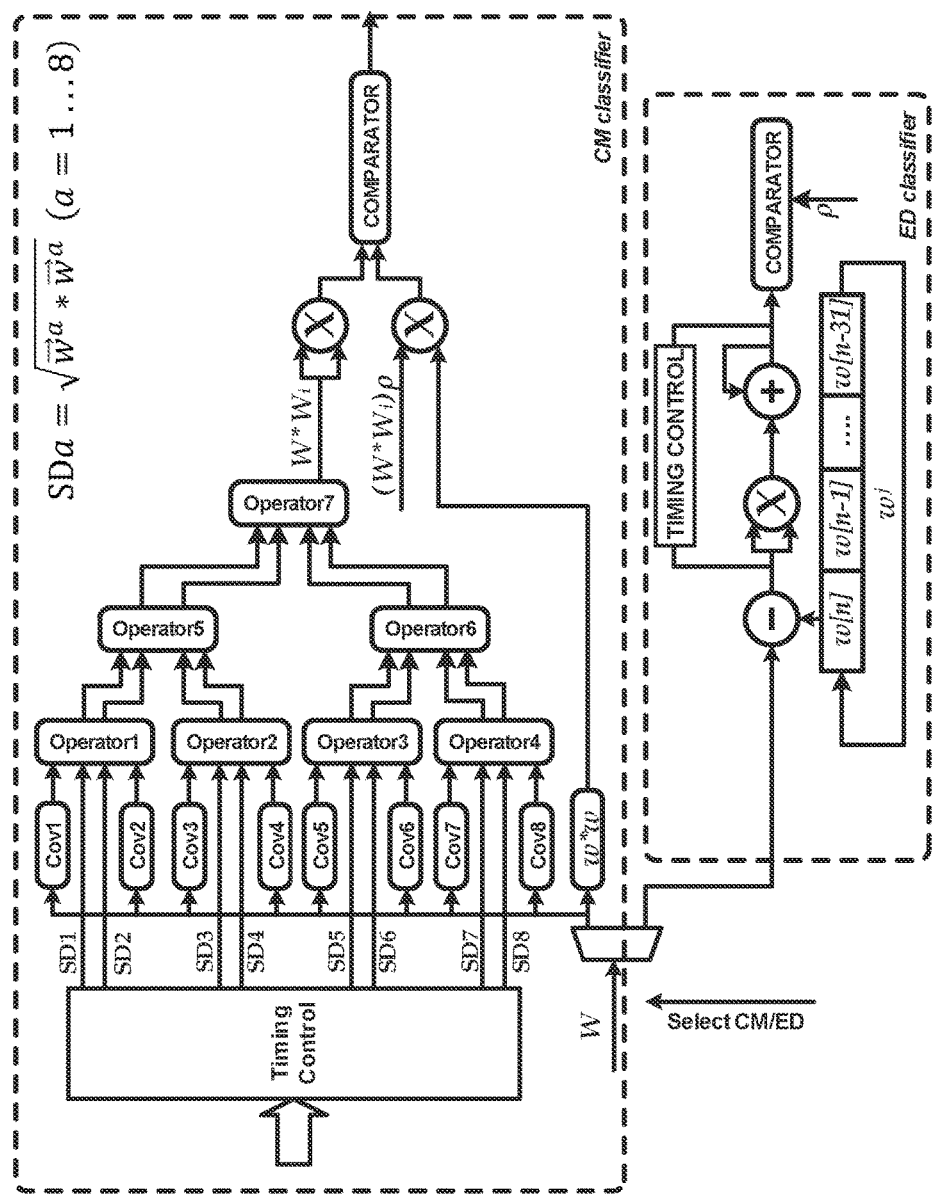

FIG. 16 illustrates a hardware implementation of the CM and ED classifiers that may be used in various embodiments of the present technology. One of the two classifiers is user-selectable through the "Select CM/ED" pin for template matching. Within the CM classifier, there are in total 8 covariance units (Cova) and 7 operator units (OperatorM) for determining the maximum correlation coefficient for the incoming spike to the eight cluster templates. The hardware implementations of the covariance units, the operator units, and the ED classifier are also shown in detail on the top two sections and the bottom section of the figure.

As shown in FIG. 16 and for each correlator, $w^i[n]$ can be first summed together and subsequently right-shifted by 5 bits (equivalently divided by $2^5=32$) to calculate the average feature $\overline{w}^i$. $w^i[n]$ was also stored in a FIFO and then subtracted by the average to calculate the difference ($w^i[n]-\overline{w}^i$). The difference can then be multiplied with the pre-calculated template difference ($w_t^a[n]-\overline{w}_t^a$), summed together, and right-shifted by 5 bit to calculate the covariance $\vec{w}^i * \vec{w}_r^a$. In order to avoid calculating the square-root in the FPGA, the comparison between two correlation coefficients ($\rho_a^i$ and $\rho_{a'}^i$) can be implemented with the expression below:

$$(\vec{w}^i * \vec{w}_t^a) \cdot (\vec{w}_t^{a'} * \vec{w}_t^{a'}) > (\vec{w}^i * \vec{w}_t^{a'}) \cdot (\vec{w}_t^a * \vec{w}_t^a) \quad (14)$$

Note that the two square-roots can be pre-calculated by the host computer using the cluster templates with no hardware implementation required. After three stages of comparison with eight comparators in total, the cluster template $\vec{w}_t^b$ best matching to the spike wavelet feature $\vec{w}^i$ can be determined. In order to screen out abnormal spike shapes—for instance two very closely timed neural spikes that are overlapping and not well-matched to any of the cluster templates, a final comparator with a user-specified rejection threshold $\rho_{th}$ can be added at the end of the calculation pipeline to reject the outlier spikes that are not suitable to assign to any one of the eight clusters:

$$(\vec{w}^i * \vec{w}_t^b)^2 > (\vec{w}^i * \vec{w}^i)(\vec{w}_t^b * \vec{w}_t^b)\rho_{th} \quad (15)$$

Spike Count Statistic Module

From the raw recording trace shown in FIG. 11, action potentials fired by a single neuron were extracted with a custom python software. Spontaneous action potential firing was significantly reduced during the three second epoch of optical illumination (green trace).

A real-time statistics unit can have implemented to perform statistical analysis at the final stage of the FPGA. The spike rates (spikes per second) of each cluster were calculated based on the output of the classifiers. Eight counters with programmable timers were added to count the spikes that were classified to one of the eight cluster groups. The calculated firing rates can also transferred back to the host computer for real-time monitoring (e.g., through the USB-UART port).

II.2 System Assessment with Published Data and Actual Neural Recording

Some embodiments of the present technology were tested using both publicly available neural spike data and pre-recorded neural data that were obtained via extracellular recordings from an anesthetized gerbil. The neural spikes in the dataset were pre-sorted and associated cluster numbers were also given, which allowed a direct comparison between the two template matching methods against different kinds of noise conditions to estimate sorting accuracies using some embodiments of the present technology. The dataset contained 23 sets of data with different degrees of signal-to-noise ratios as well as both Gaussian (20 sets) and non-Gaussian (3 sets) noise contaminations.

A previously recorded extracellular voltage trace obtained with a high-impedance Tungsten metal electrode (WEPT33.0B10, MicroProbes, Gaithersburg, Md., USA) placed into the fifth nerve (trigeminal) nerve tract within the brain stem of an anesthetized Mongolian gerbil (*Merion's unguiculates*) was also used to assess the performance. All experimental procedures complied with all applicable laws and National Institutes of Health guidelines and were approved by the University of Colorado Institutional Animal Care and Use Committee (IACUC).

VI. EXPERIMENTAL RESULTS

In this section, experimental results based on a publicly available dataset and private neural data recorded from an anesthetized Mongolian gerbil were used to evaluate the performance of some embodiments of the technology.

III.1 Performance of the FPGA Real-Time Module

Figure 17:
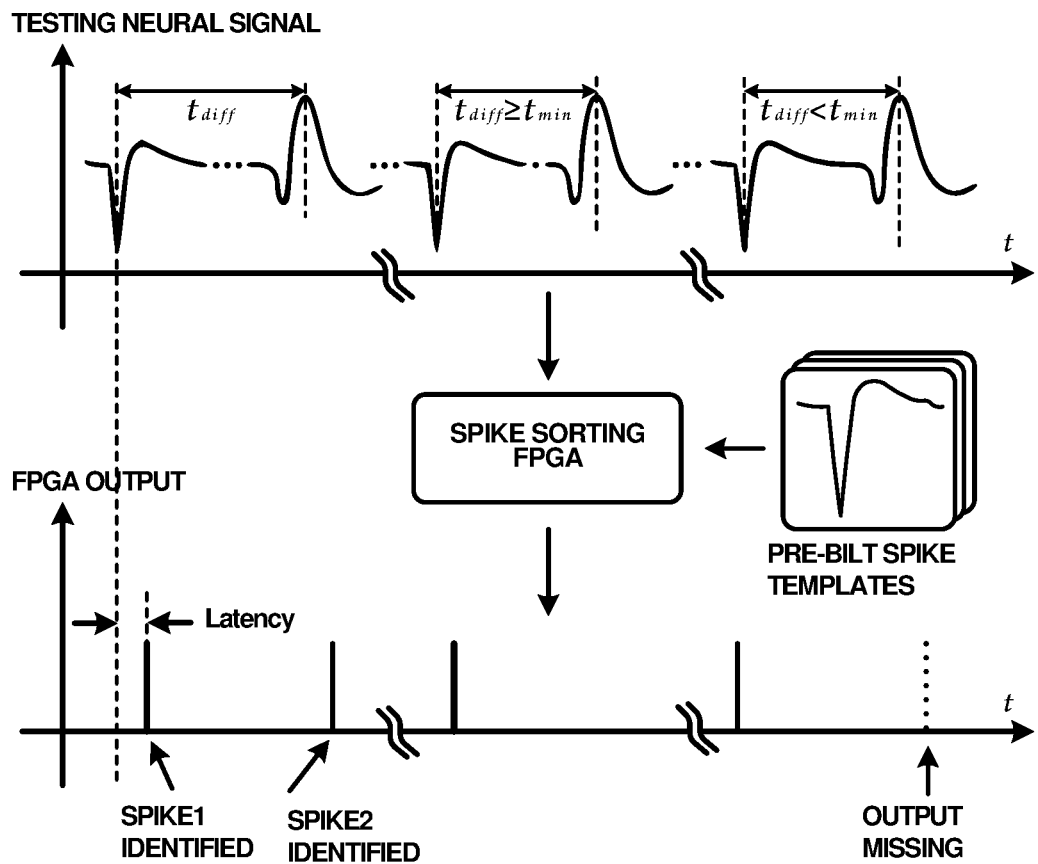
FIG. 17 illustrates two neural spikes extracted from the neural recording of a gerbil were pieced together with a peak time difference to measure the maximum spike sorting rate of the FPGA.

The maximum spike sorting rate was first measured to characterize the FPGA performance. The maximum spike sorting rate was measured by monotonically reducing the temporal difference between the peaks of two spikes until the FPGA module can no longer differentiate the second spike from the first spike for sorting. Two neural spikes each with a data length of 32 bytes were selected from the previously recorded gerbil neural data and the two spikes were pieced together with a varying time difference $t_{diff}$, as shown in FIG. 17.

If the temporal spacing between the two spikes was larger than the 32 byte span of the spikes, additional data points with no spike features were padded in the gap space, and if the spacing was less than the span, the data points of the overlapping space were averaged between the two spikes. The FPGA module was implemented with a digital output to indicate the successful sorting of the input spikes. Since the neural data was measured with a sampling rate of 24 kHz and if the two 32-byte neural spikes were connected together back-to-back with no temporal padding, i.e., $t_{diff}$=1.33 ms, a 750 spikes/second sorting rate will be obtained (Note that the spike itself is less than 32 bytes). But this number is not the maximum sorting rate for some embodiments because the system can actually handle neural spikes that are more closely spaced together.

In order to estimate the maximum sorting rate, the time difference between the two spikes was further reduced to allow overlaps, and the measured results indicated that when the time difference between the two pulses was less than 1.06 ms ($t_{min}$=1.06 ms), the second spike was no longer sorted by the FPGA module, indicating that the two pulses were too closed to be separated. Thus, the maximum spike sorting rate of the FPGA module was determined to be 941 spikes/second for the tested embodiments.

The latency of analyzing the neural spikes for the FPGA module was also estimated and the data processing time for each of the sub-processing units are listed in Table I.

TABLE I

System Latency of the FPGA real-time spike sorting module

| FPGA sub-processing units | Clock cycles | | Latency (μs) |
|---|---|---|---|
| | Sampling (24 KHz) | Processing (100 MHz) | |
| Data smoothing | 4 | 2 | 166.7 |
| NEO peak detection | 1 | 2 | 41.7 |
| Spike isolation | 42 | 32 | 1750.3 |
| Haar transformation | NA | 58 | 0.58 |
| Template matching | NA | 72 | 0.72 |
| Firing rate statistics | NA | 2 | 0.02 |
| Total latency | 47 | 168 | 1960.0 |

Comparatively, the sampling frequency (using an external analog-to-digital converter) in digitizing the neural voltage is 24 KHz, or 41.7 μs/sample, while the FPGA system clock frequency is 100 MHz, or 0.01 μs/clock, for data processing and calculations. Since the FPGA clock frequency is significantly higher than the sampling frequency, most of the latency resulted from the wait time for enough data points to perform the sorting. Here the estimation of the system latency is briefly described.

For the latency of data smoothing, an 8 point average filter was used in which the filter was required to wait for 4 additional digitized samples to be loaded to the filter before it could perform the smoothing calculation of the current data point. In addition, 2 additional FPGA processing clock cycles were required to calculate the average. Thus, the total processing time for the smoothing was 166.7 μs.

For peak detection, the NEO algorithm was required to wait for 1 additional sample and 2 FPGA processing cycles for the calculation, which is equivalent to a latency of 41.7 μs. The spike isolation module was the most time-consuming module in the tested embodiments and thus was the dominant contributor to the system latency. The module needs 32 sampling cycles to store the entire spike to its FIFO as well as another 10 additional samples to allow alignment of spikes with uneven spike shapes to the array center, and also required 32 FPGA processing clock cycles for the spike readout, which translates to a latency of 1750.3 μs.

After the neural spike was isolated to 32 byte data, no additional data waiting was needed for the processes of Haar transformation, template matching and firing rate calculation, resulting in a relatively short processing latency. For the Haar transformation, template matching and statistic calculations, 58, 72 and 2 FPGA processing cycles were required and the corresponding processing time was only 0.58, 0.75, and 0.02 μs, which were almost negligible. Therefore, the total sampling and processing clock cycles of all the sub-processing units were 47 and 168, which attributed to a total system latency of ~1.96 ms. If the input signal already has a high SNR, the smoothing module can be bypassed by the users and the system latency could further be reduced to ~1.79 ms. This latency result was also confirmed with simulations with ModelSim (Mentor Graphics, Wilsonville, Oreg.) included in Vivado at the gate level.

For the use of the FPGA resource, the implementation used about 65% of the FPGA slice look-up tables (slice LUTs). Additionally, the amount of slice registers, block memories and bonded input-output blocks (IOBs) were accounted to be 14.5%, 9% and 13.3% of the total available resources respectively.

III.2 Spike Sorting Accuracy Comparing CM and ED Using Public Supervised Data

The sorting accuracy of the FPGA module was also evaluated using publicly available neural recording data. Cluster classification of both CM and ED were evaluated to illustrate the difference between the two techniques. The information gives an indication of which technique is best to use under certain experimental conditions for optimal sorting.

Twenty-three sets of artificial neural spike trains contaminated with different types of noise and fluctuations were used to test the FPGA module. Among the 23 sets of data, 20 sets of the data contain artificial neural spikes contaminated with different degrees of Gaussian noise and the final 3 sets of data are corrupted by non-Gaussian spike height fluctuation. For the 20 sets of data contaminated by Gaussian noise (where σ in FIG. 5 denotes the standard deviation of the Gaussian noise function), 12 data sets (8 for EasyGroup1 and 4 for EasyGroup2) were constructed by easily separable neural spikes and 8 sets of data (4 for DifficultGroup1 and 4 for DifficultGroup2) were constructed by neural spikes having very similar temporal shapes. The 3 non-Gaussian fluctuation groups were constructed to mimic spike height changes due to various physiological conditions (electrode drifting, cell bursting activity, and local field potentials). Regarding the nature of contamination, all the data sets are supervised and are pre-labeled with predetermined cluster groups, which allows us to compare the sorting results from the FPGA to calculate the sorting accuracy.

Figure 18:
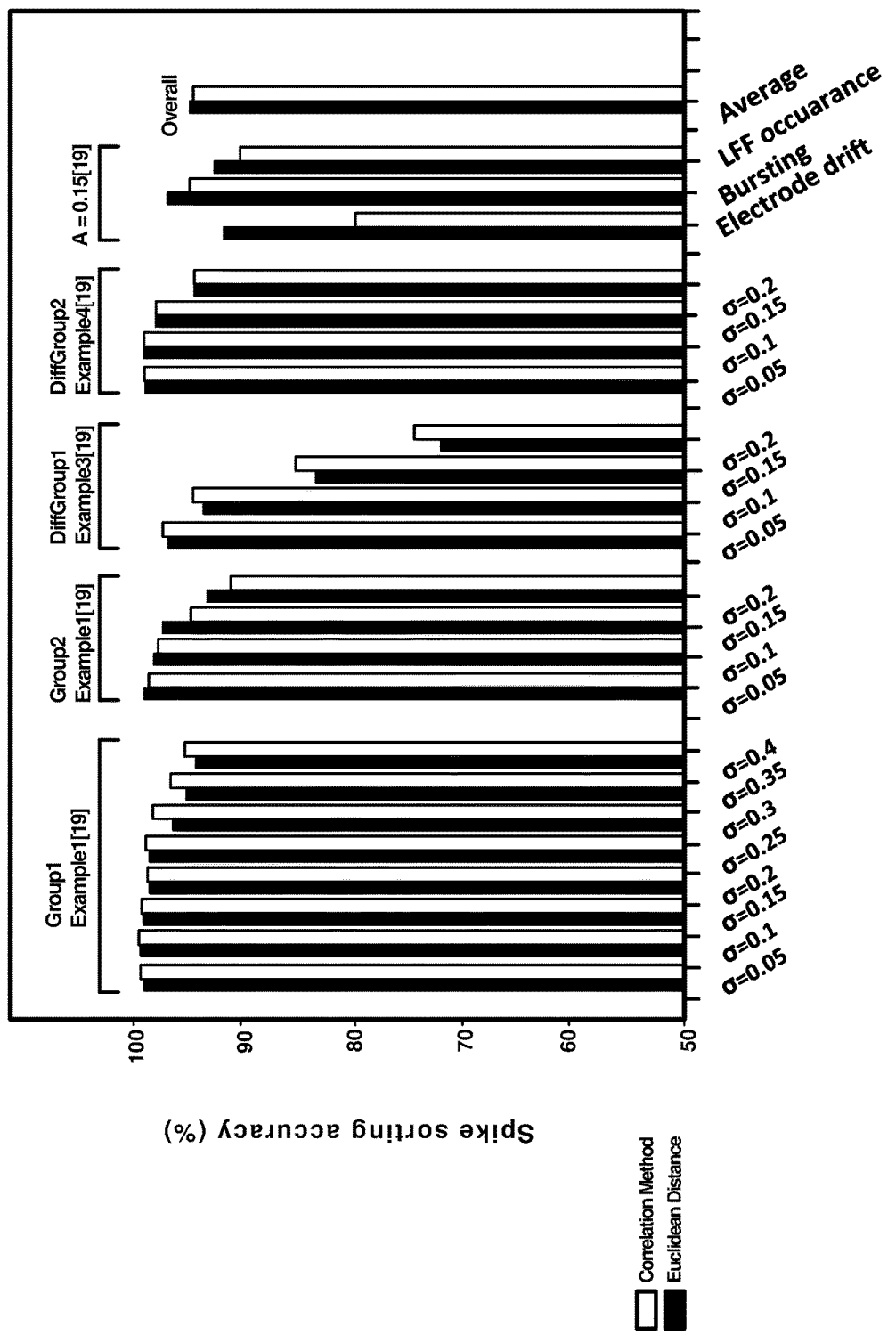
FIG. 18 is a bar chart illustrating the sorting accuracy of both CM and EM against the 23 data sets.

FIG. 18 is a bar chart illustrating the sorting accuracy of both CM and EM against the 23 data sets. Here, sorting accuracy is defined as the ratio between the number of spikes that are correctly clustered against the total numbers of spikes. Testing among the 23 sets of data, CM showed a slightly better (1%) overall sorting accuracy than ED. Looking more closely at the sorting results, for the 20 sets of data that are contaminated by Gaussian noise (first four groups in FIG. 18), ED was actually performing slightly better than CM and the accuracy difference was only about 2%. On the other hand, for the 3 sets of non-Gaussian fluctuation, CM had a significantly better sorting accuracy than that of ED, especially for one set of data that simulated amplitude fluctuation caused by the positional drifting of the metal electrode within the brain during long duration experiments. Under this particular experimental condition, ED had about 80% sorting accuracy while CM could achieve a sorting accuracy as high as 92% (a 12% accuracy enhancement).

Figure 19A:
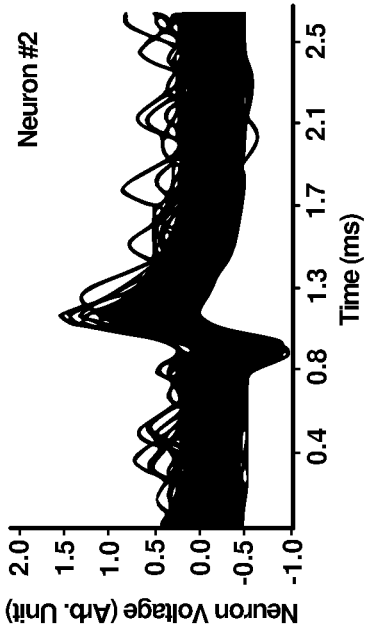
FIGS. 19A-19J illustrates a comparison between CM and ED in spike sorting using neural spikes artificially constructed to simulate electrode drifting.
Figure 19B:
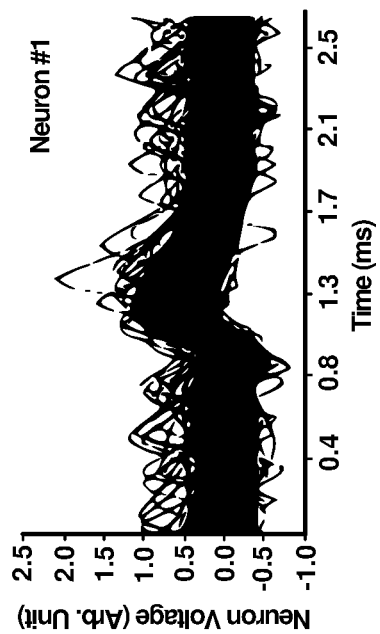

FIG. 19A illustrates an example neural voltage trace recorded from an anesthetized gerbil. The top stars and triangles indicate the corresponding cluster groups of the spikes underneath. In FIG. 19B, temporal profiles of the two cluster templates generated by the host computer using SPC. A phase plot of the two cluster groups (stars and triangles) with each marker representing a neural spike is presented in 19C. FIG. 19D shows the firing rates of the two clusters calculated over the 100 s neural data by the FPGA system for testing with both CM and ED template matching.

Figure 19C:
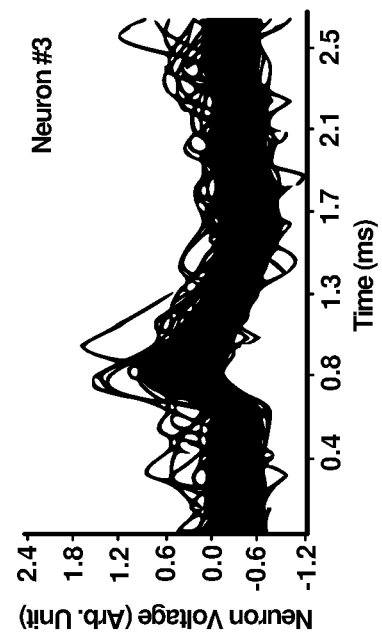
Figure 19D:
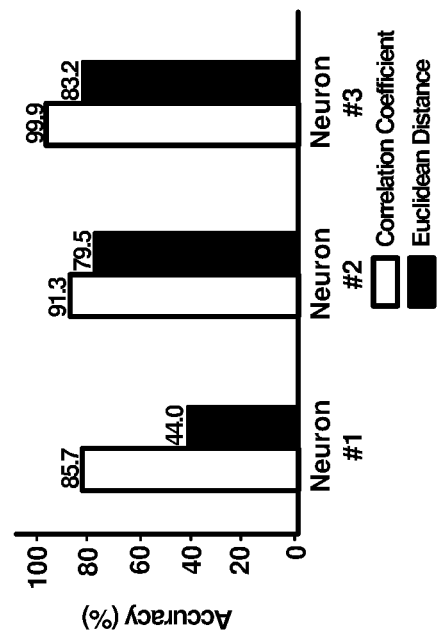
Figure 19E:
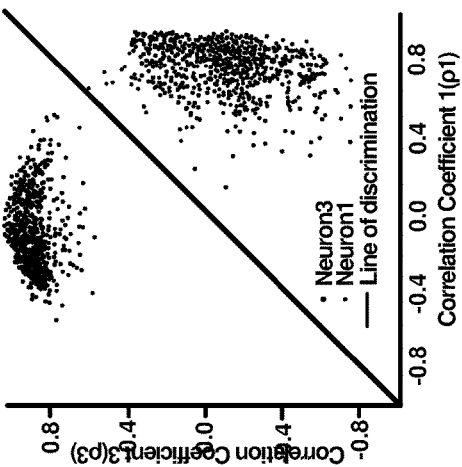
Figure 19F:
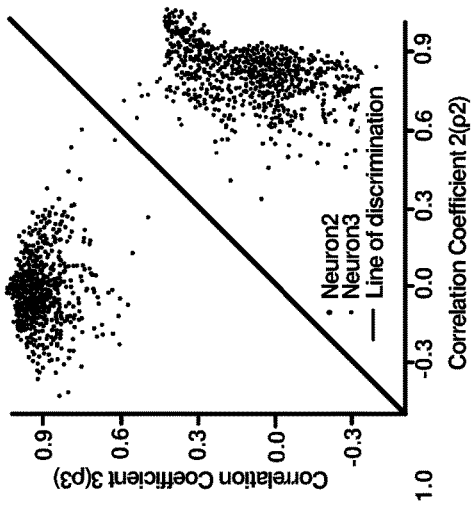
Figure 19G:
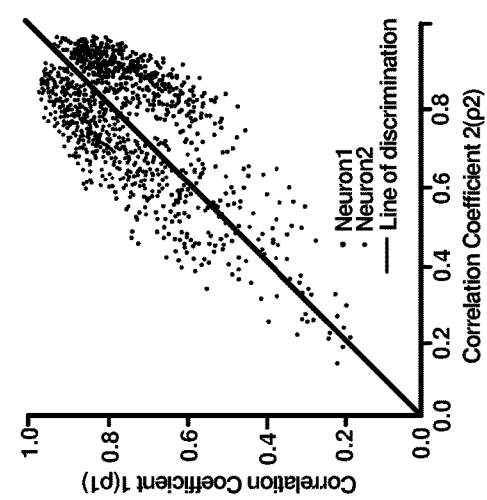
Figure 19H:
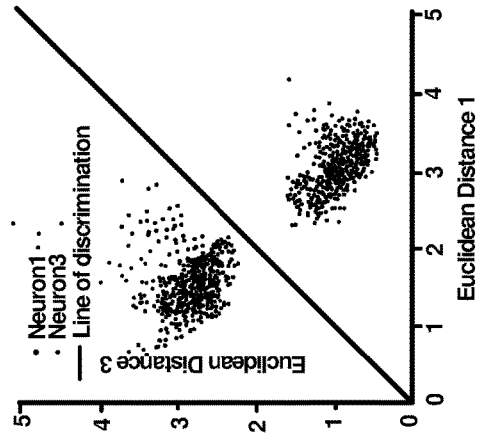
Figure 19I:
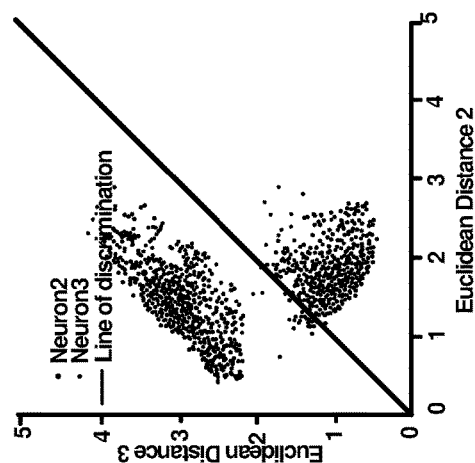
Figure 19J:
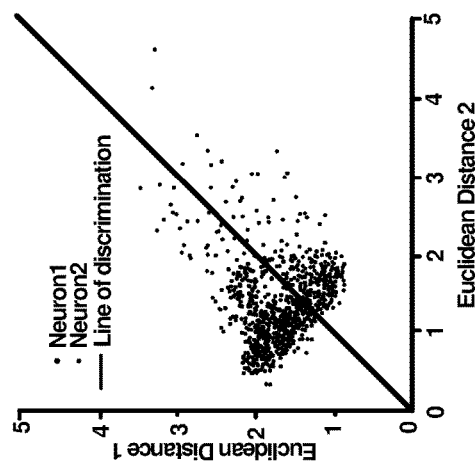

The temporal profiles of the three cluster groups with the artificially varying amplitudes are shown in FIGS. 19A-19C. FIG. 19D shows the sorting accuracy of this test data set using both CM and ED template matching methods. It is evident that ED has inferior performance than CM for all three cluster groups. To better understand the results, the correlation coefficients of any two cluster groups were plotted against one another in FIG. 19E-19F, and the Euclidean distances of any two groups are also plotted in FIG. 19H-19J. For the CM figures, it is apparent that spike clusters were cleanly separated by the diagonal line and the clusters stayed in their own quadrants, either in the upper or lower quadrants. In contrast, for ED, the two cluster groups in FIG. 19H were intermingled, and the lower cluster groups intrude into the upper quadrant in FIG. 19I. These results can be explained by the fact that mathematically, the correlation coefficient is much less sensitive to amplitude fluctuation as long as the spike shape is maintained while Euclidean distance can change relatively significant when the amplitude varies. The results also indicate that separating cluster groups in CM can be achieved by using simple diagonal lines to separate the cluster quadrants. In contrast, although several prior studies have used diagonal lines to separate clusters, this is evidently not an optimal technique and more sophisticated comparison algorithms based on cluster boundary segmentation are perhaps required to yield better cluster results for ED.

Figure 20A:
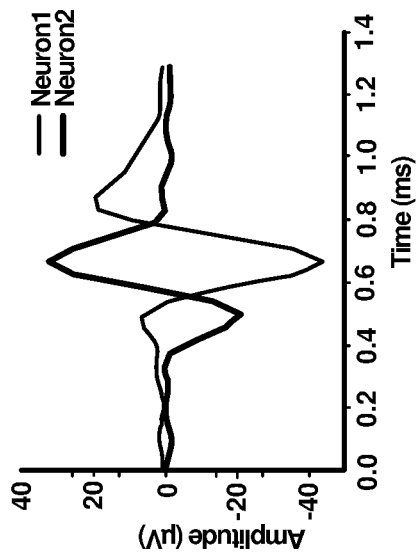
FIGS. 20A-20D illustrates neural voltages containing two distinct types of pikes originating from two close-by neurons as identified by some embodiments of the present technology.
Figure 20B:
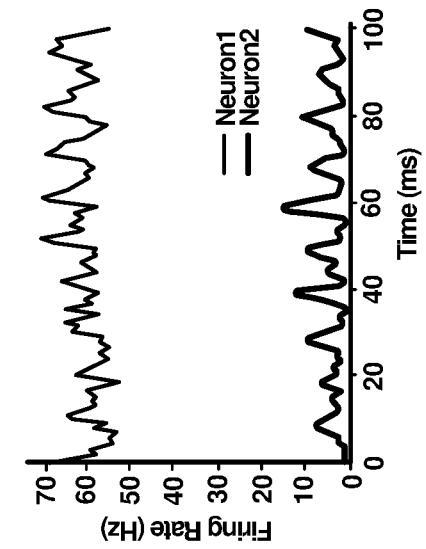
Figure 20C:
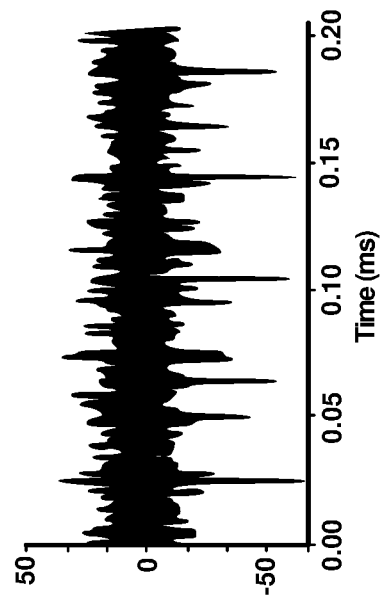
Figure 20D:
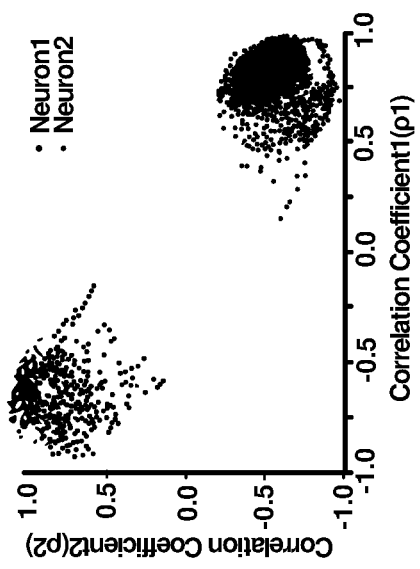

III.3 Spike Sorting Accuracy Evaluated by Recorded Neural Spikes of an Anesthetized Gerbil FIG. 20A shows a portion (0.5 s) of the raw neural voltage recorded from the Mongolian gerbil (the entire recording was 120 s). The neural voltage contained two distinct types of spikes originating from two close-by neurons that have been identified by the system. FIG. 20B shows the averaged temporal profiles of the two cluster templates estimated by the SPC algorithm on the host computer, and the template creation used about 20 s, or 16.6%, of the recorded data. The cluster features were then transferred to the FPGA for sorting the rest of the data. FIG. 20C is the sorted result using CM and represented by a correlational plot of Pearson's corrélation coefficients $\rho_a^i$ of the two groups. The neural spikes were highly clustered into two groups distanced away from each other, indicating that the spikes were well separated. Finally, FIG. 20D shows the two time traces of the firing rates of the two cluster groups over the 100 s period. The first neuron maintains a higher firing rate of about 50 to 70 pulses/second, in contrast to the second neuron that fired less than 10 pulses/second for the entire recording.

VII. DISCUSSION

Various embodiments of the present technology provide for a real-time rapid neural spike sorting system by matching neural spikes to a group of pre-calculated cluster templates. One goal of this development was to reduce the sorting time by eliminating the needs of performing sophisticated spike sorting calculations for every single spike, but instead using a host computer to pre-calculate cluster templates to allow rapid sorting by comparing incoming spikes to the templates. With this technique, the system achieves a maximum sorting rate of 941 spikes/second and a sorting latency of less than 2 ms. This performance is approaching the physiological time characteristics of a neural spike, which has a pulse width of about 1 ms.

In addition, the various embodiments of the system are flexible by using two kinds of template matching techniques, either through finding the shortest Euclidean distance or the smallest correlation coefficient among the templates. These two methods are selectable by users to fit different experimental sorting needs. Various results indicate that both techniques achieve good sorting accuracies. While ED has a slight edge (about 2% better) over CM for sorting spikes contaminated with Gaussian fluctuation, CM can achieve much better accuracy for pulses that are changing over slow drift of the electrode position in behavioral experiments. These results provide a guideline for choosing the appropriate template matching technique to achieve the best sorting accuracies according to the actual experimental conditions.

Closed-loop neural control is a general technical term referring to interventions of the neural circuit by analyzing responses, either firing rates from electrophysiology recording or behavioral responses of the test subject, of the neural system on the fly. Closed-loop control provides an exciting opportunity for neuroscience research and engineering communities to look into neural systems not only from a passive observational position; but also from an active control standpoint. To that end; the biochemical technique of optogenetics provides a precise control method that was not available a decade ago. Optogenetics allows researchers to stimulate or inhibit a neural system selectively, or simultaneously stimulate and inhibit a neural network.

Moreover, with proper biochemical techniques, a specific cell type within the neural target can be specifically or exclusively controlled. Thus combining optogenetics with feedback control, recent experiments have demonstrated the firing rate of a neuron can be locked for a short period of time. These recent developments provide a good reason for development of rapid spike sorting methods. For instance, the output, such as the firing rate, of rapid spike sorting can perhaps be used as the inputs for the closed-loop control routines. In these closed-loop control schemes, the inputs have to be "instantaneous" to reflect the current state of the neural system; thus rapid sorting and short latency of analyzing neural spikes becomes important criteria.

When an electrode was inserted into the brain to measure neural voltages, several different kinds of perturbations can contaminate the measured signal. The most common contamination is thermal noise induced by the electrode impedance as well as the intrinsic noise of the amplifier. Since these noises are stochastic in nature, their noise distributions are typically Gaussian. As shown by current results, ED and CM can handle Gaussian noise almost equally well and the sorting accuracies are good even for low signal-to-noise ratio situations. Besides Gaussian contaminations, there are also other types of contaminations that are more related to the physiological conditions of the neural system, such as large local field potential riding on top of weak action potentials. Particularly, for long-term extracellular in vivo recording where the animal was allowed to be moving freely, minute movements of the electrodes can change the impedances between the electrodes and the neurons, causing the amplitudes of the spikes to fluctuate without changing the overall temporal shapes. Under this scenario, CM has much improved performance over ED since CM is not sensitive to the amplitude change due to the inherent normalization to the signal. In contrast, ED strictly measured the distance between two points in phase space and this distance can change rather substantially as the spike amplitude fluctuates. Another advantage of CM is that cluster decimation is relatively simple through disseminating of the diagonal line, which could further simplify the implementation of CM over ED at the hardware level.

In various embodiments, the maximum sorting rate was measured to be 941 spikes/second with a sorting latency of less than 2 ms. Both numbers are not limited by the processing power of the FPGA or the template matching algorithm, but simply reflect the temporal nature of the neural spikes. Physiologically speaking, a neural spike has a pulse width of ~1 to 2 ms and a neuron typically cannot fire more than several hundred of spikes per second, both of which are limited by the molecular dynamics of the Na and K ion channels. Thus, using an analog-to-digital converter with higher sampling frequency will not help improving the sorting rate simply because the sorting cannot occur without the entire spike being sampled. For this reason, various embodiments of the current technology approach the limits of how fast a system can be in sorting neural spikes, at least in the case of single channel sorting, unless non-causal techniques are developed to predict spike profiles.

Various embodiments of the present technology include feature extraction before the matching and also allows users to select either ED or CM for the matching. In addition, some embodiments also include a real-time statistical module to calculate the instantaneous firing rates while other systems do not have this capability. The real-time statistical module may open up the possibility in the future for closed-loop neural control based on using instantaneous firing rates as control inputs. Regarding the system performance, the signal paths of all the necessary processing steps have been optimized to allow maximum output speed. This optimization allows some embodiments to achieve an overall system latency of 1.96 ms, as well as a fast spike sorting rate of 941 spikes/second. Some embodiments can include single or multiple recording channels.

VIII. EXEMPLARY COMPUTER

Aspects and implementations of the system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 21:
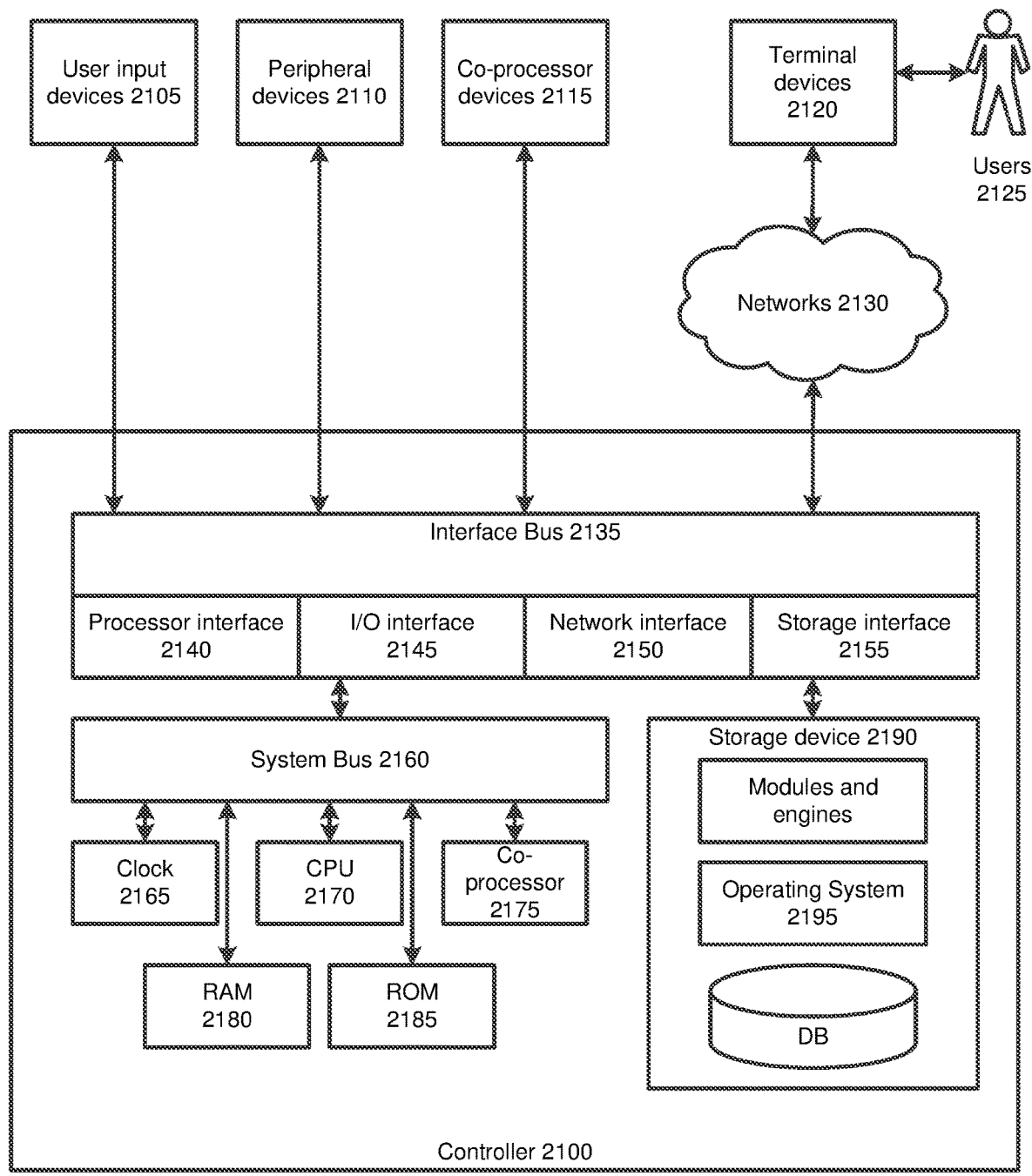
FIG. 21 is a block diagram illustrating an example machine representing the computer systemization that may be used in various embodiments of the present technology.

FIG. 21 is a block diagram illustrating an example machine representing the computer systemization. The host computer system 2100 may be in communication with entities including one or more users 2125 client/terminal devices 2120, user input devices 2105, peripheral devices 2110, an optional co-processor device(s) (e.g., cryptographic processor devices) 2115, and networks 2130 (e.g., 115 in FIG. 1). Users may engage with the host computer system 2100 via terminal devices 2120 over networks 2130.

Computers may employ central processing unit (CPU) or processor to process information. Processors may include programmable general-purpose or special-purpose microprocessors, programmable controllers, application-specific integrated circuits (ASICs), programmable logic devices (PLDs), embedded components, combination of such devices and the like. Processors execute program components in response to user and/or system-generated requests. One or more of these components may be implemented in software, hardware or both hardware and software. Processors pass instructions (e.g., operational and data instructions) to enable various operations.

The host computer system 2100 may include clock 2165, CPU 2170, memory such as read only memory (ROM) 2185 and random access memory (RAM) 2180 and co-processor 2175 among others. These controller components may be connected to a system bus 2160, and through the system bus 2160 to an interface bus 2135. Further, user input devices 2105, peripheral devices 2110, co-processor devices 2115, and the like, may be connected through the interface bus 2135 to the system bus 2160. The interface bus 2135 may be connected to a number of interface adapters such as processor interface 2140, input output interfaces (I/O) 2145, network interfaces 2150, storage interfaces 2155, and the like.

Processor interface 2140 may facilitate communication between co-processor devices 2115 and co-processor 2175. In one implementation, processor interface 2140 may expedite encryption and decryption of requests or data. Input output interfaces (I/O) 2145 facilitate communication between user input devices 2105, peripheral devices 2110, co-processor devices 2115, and/or the like and components of the controller 2100 using protocols such as those for handling audio, data, video interface, wireless transceivers, or the like (e.g., Bluetooth, IEEE 1394a-b, serial, universal serial bus (USB), Digital Visual Interface (DVI), 802.11a/b/g/n/x, cellular, etc.). Network interfaces 2150 may be in communication with the network 2130. Through the network 2130, the host computer system 2100 may be accessible to remote terminal devices 2120. Network interfaces 2150 may use various wired and wireless connection protocols such as, direct connect, Ethernet, wireless connection such as IEEE 802.11a-x, and the like.

Examples of network 2130 include the Internet, Local Area Network (LAN), Metropolitan Area Network (MAN), a Wide Area Network (WAN), wireless network (e.g., using Wireless Application Protocol WAP), a secured custom connection, and the like. The network interfaces 2150 can include a firewall which can, in some aspects, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including, for example, the access and operation rights of an object by an individual, a machine, and/or an application, and the circumstances under which the permission rights stand. Other network security functions performed or included in the functions of the firewall, can be, for example, but are not limited to, intrusion-prevention, intrusion detection, next-generation firewall, personal firewall, etc., without deviating from the novel art of this disclosure.

Storage interfaces 2155 may be in communication with a number of storage devices such as, storage devices 2190, removable disc devices, and the like. The storage interfaces 2155 may use various connection protocols such as Serial Advanced Technology Attachment (SATA), IEEE 1394, Ethernet, Universal Serial Bus (USB), and the like.

User input devices 2105 and peripheral devices 2110 may be connected to I/O interface 2145 and potentially other interfaces, buses and/or components. User input devices 2105 may include card readers, finger print readers, joysticks, keyboards, microphones, mouse, remote controls, retina readers, touch screens, sensors, and/or the like. Peripheral devices 2110 may include antenna, audio devices (e.g., microphone, speakers, etc.), cameras, external processors, communication devices, radio frequency identifiers (RFIDs), scanners, printers, storage devices, transceivers, and/or the like. Co-processor devices 2115 may be connected to the controller 2100 through interface bus 2135, and may include microcontrollers, processors, interfaces or other devices.

Computer executable instructions and data may be stored in memory (e.g., registers, cache memory, random access memory, flash, etc.) which is accessible by processors. These stored instruction codes (e.g., programs) may engage the processor components, motherboard and/or other system components to perform desired operations. The host computer system 2100 may employ various forms of memory including on-chip CPU memory (e.g., registers), RAM 2180, ROM 2185, and storage devices 2190. Storage devices 2190 may employ any number of tangible, non-transitory storage devices or systems such as fixed or removable magnetic disk drive, an optical drive, solid state memory devices and other processor-readable storage media, Computer-executable instructions stored in the memory may include one or more program modules such as routines, programs, objects, components, data structures, and so on that perform particular tasks or implement particular abstract data types. For example, the memory may contain operating system (OS) component 2195, modules and other components, database tables, and the like. These modules/components may be stored and accessed from the storage devices, including from external storage devices accessible through an interface bus.

The database components can store programs executed by the processor to process the stored data. The database components may be implemented in the form of a database that is relational, scalable and secure. Examples of such database include DB2, MySQL, Oracle, Sybase, and the like. Alternatively, the database may be implemented using various standard data-structures, such as an array, hash, list, stack, structured text file (e.g., XML), table, and/or the like. Such data-structures may be stored in memory and/or in structured files.

The controller 2100 may be implemented in distributed computing environments, where tasks or modules are performed by remote processing devices, which are linked through a communications network, such as a Local Area Network ("LAN"), Wide Area Network ("WAN"), the Internet, and the like. In a distributed computing environment, program modules or subroutines may be located in both local and remote memory storage devices. Distributed computing may be employed to load balance and/or aggregate resources for processing. Alternatively, aspects of the host computer system 2100 may be distributed electronically over the Internet or over other networks (including wireless networks). Those skilled in the relevant art(s) will recognize that portions of the system may reside on a server computer, while corresponding portions reside on a client computer. Data structures and transmission of data particular to aspects of the controller 2100 are also encompassed within the scope of the disclosure.

IX. CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to," As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A device comprising:
    an integrated circuit including:
        a neural amplifier to receive signals from one or more optrodes measuring target neurons,
            wherein the signals measuring the target neurons include measurements of action potentials or local field potentials; and
        an optical driver to control an optical source to provide optogenetic stimulation or inhibition of the target neurons.

2. The device of claim 1, wherein the neural amplifier includes multiple stages with a unity-gain buffer to maximize input impedance from the signals received via the one or more optrodes.

3. The device of claim 1, wherein the optical driver includes a single or a multi-stage current driver that includes a first stage to provide coarse control and a second stage to provide fine control.

4. The device of claim 1, wherein the optical driver includes a laser driver or a light emitting diode driver.

5. The device of claim 1, further comprising a real-time spike sorting unit configured to use template matching techniques to sort the signals from the one or more optrodes based on spikes.

6. The device of claim 5, further comprising a communication interface to receive templates created external to the integrated circuit.

7. The device of claim 1, further comprising a real-time spike sorting unit that includes multiple template matching processes implemented in hardware on the integrated circuit that can be selectively activated by a user.

8. The device of claim 1, wherein the multiple template matching processes include a Euclidian distance matching process and a correlational matching process.

9. A method of operating a system having an integrated circuit, the method comprising:
    measuring, using one or more recording electrodes connected to the integrated circuit, neural activity of a brain of an animal or human;
    processing the neural activity measured using the one or more recording electrodes to identify neuron firing;
    determining, using a controller of the integrated circuit, a control action to repattern the neuron firing; and
    implementing the control action in the brain of the animal or human using an optogenetic control system.

10. The method of claim 9, further comprising identifying and sorting spikes within the neural activity measured using the one or more recording electrodes.

11. The method of claim 10, further comprising using template classification to identify neural activity from different neurons.

12. The method of claim 11, wherein the template classification includes multiple user-selectable options that include a Euclidian distance matching process and a correlational matching process.

13. The method of claim 9, further comprising:
    receiving, at the integrated circuit and from an external computer, a set of cluster templates to a field programmable gate array (FPGA) or an application-specific integrated circuit (ASIC);
    sorting, using the FPGA or ASIC, spikes within the neural activity based on the set of cluster templates;
    generating sorted neural activity based on the spikes identified locally at the integrated circuit; and
    feeding, to the controller, the sorted neural activity that can be used, at least in part, in determining the control action to repattern the neuron firing.

14. The method of claim 9, wherein implementing the control action in the brain of the animal also includes non-optical manipulation.

15. A system comprising:
    a power supply;
    one or more processors;
    an integrated circuit;
    a neural interface to receive, via one or more electrodes coupled to the integrated circuit, measurements of neural activity from a brain of an animal or human; and
    a memory having stored thereon instructions that when executed by the one or more processors cause the system to:
        process the measurements of the neural activity from the brain of the animal or human to identify neuron firing;
        determining, using a controller of the integrated circuit, a control action to alter the neuron firing; and
        transmitting the control action to an optogenetic laser system to facilitate inhibition or stimulation of neuron firing.

16. The system of claim 15, further comprising a field programmable gate array (FPGA) or an application-specific integrated circuit (ASIC) configured to receive the measurements of the neural activity and programmed to sort spikes within the measurements of the neural activity.

17. The system of claim 15, further comprising an optrode having the one or more electrodes that can be inserted into the brain of the human or animal to collect the measurements of the neural activity that can be transmitted to the neural interface.

18. The system of claim 15, wherein the optogenetic laser system includes a single or multi-stage current controller to translate the control action into a desired light to facilitate the inhibition or stimulation of neuron firing.

19. The system of claim 15, further comprising an external computer to generate a set of cluster templates.

20. The system of claim 19, further comprising a field programmable gate array (FPGA) or an application-specific integrated circuit (ASIC) to use the set of cluster templates to classify, in real-time, spikes within the measurements of the neural activity and separate measurements from different neurons.

* * * * *